United States Patent
Saito et al.

(10) Patent No.: US 9,415,638 B2
(45) Date of Patent: Aug. 16, 2016

(54) DECORATIVE TIRE AND METHOD FOR PRODUCING SAME

(71) Applicants: DNP Fine Chemicals Co., Ltd., Yokohama-shi, Kanagawa (JP); Bridgestone Corporation, Tokyo (JP)

(72) Inventors: Yasuma Saito, Yokohama (JP); Toshio Furutaka, Yokohama (JP); Yukio Sugita, Yokohama (JP); Yuki Nakamura, Kodaira (JP); Kojiro Torisu, Kodaira (JP); Akihiko Hajikano, Kodaira (JP)

(73) Assignee: Bridgestone Corporation, Tokyo (JP)

( * ) Notice: Subject to any disclaimer, the term of this patent is extended or adjusted under 35 U.S.C. 154(b) by 0 days.

(21) Appl. No.: 14/371,390

(22) PCT Filed: Jan. 11, 2013

(86) PCT No.: PCT/JP2013/050471
§ 371 (c)(1),
(2) Date: Jul. 9, 2014

(87) PCT Pub. No.: WO2013/105662
PCT Pub. Date: Jul. 18, 2013

(65) Prior Publication Data
US 2015/0010737 A1   Jan. 8, 2015

(30) Foreign Application Priority Data
Jan. 12, 2012 (JP) .................... 2012-004527

(51) Int. Cl.
| | |
|---|---|
| *B32B 3/02* | (2006.01) |
| *B60C 13/00* | (2006.01) |
| *B41J 2/01* | (2006.01) |
| *C09D 133/04* | (2006.01) |
| *C09D 11/101* | (2014.01) |
| *C09D 11/30* | (2014.01) |
| *G01N 3/08* | (2006.01) |
| *B60C 1/00* | (2006.01) |
| *B41M 5/00* | (2006.01) |

(52) U.S. Cl.
CPC ............ *B60C 13/001* (2013.04); *B41J 2/01* (2013.01); *B60C 1/0025* (2013.04); *B60C 13/00* (2013.01); *C09D 11/101* (2013.01); *C09D 11/30* (2013.01); *C09D 133/04* (2013.01); *G01N 3/08* (2013.01); *B41M 5/0047* (2013.01); *B41M 5/0064* (2013.01); *Y10T 428/24802* (2015.01); *Y10T 428/24851* (2015.01)

(58) Field of Classification Search
CPC ...... B60C 13/001; B60C 13/00; C09D 11/30; C09D 11/101; B41J 2/01; B41M 5/0047; B41M 5/064; Y10T 428/24802; Y10T 428/24851
See application file for complete search history.

(56) References Cited

U.S. PATENT DOCUMENTS

| | | | |
|---|---|---|---|
| 5,763,048 A | 6/1998 | Takahashi | |
| 5,852,095 A | 12/1998 | Yamauchi et al. | |
| 2004/0024078 A1 | 2/2004 | Itoh et al. | |
| 2004/0099170 A1 | 5/2004 | Takabayashi | |
| 2009/0171007 A1 | 7/2009 | Jonai et al. | |
| 2009/0291225 A1* | 11/2009 | Takabayashi | .......... B41J 11/002 427/487 |
| 2011/0028586 A1 | 2/2011 | Kito et al. | |
| 2011/0200794 A1 | 8/2011 | Kida et al. | |
| 2011/0230582 A1 | 9/2011 | Kito et al. | |

FOREIGN PATENT DOCUMENTS

| | | |
|---|---|---|
| EP | 0757059 A1 | 2/1997 |
| EP | 1178064 A1 | 2/2002 |
| EP | 1388578 A1 | 2/2004 |
| EP | 1625952 A1 | 2/2006 |
| EP | 2277956 A1 | 1/2011 |
| EP | 2351799 A1 | 8/2011 |
| JP | H08-003409 | 1/1996 |
| JP | H083409 A | 1/1996 |
| JP | 2004131725 A | 4/2004 |
| JP | 2006-274053 A | 10/2006 |
| JP | 2009-280070 A | 12/2009 |
| JP | 2010125440 A | 6/2010 |
| JP | 2010132827 A | 6/2010 |

(Continued)

OTHER PUBLICATIONS

Extended European Search Report dated Aug. 20, 2015 for European Application No. 13735691.1.

(Continued)

*Primary Examiner* — Elizabeth Mulvaney
(74) *Attorney, Agent, or Firm* — Locke Lord LLP; James E. Armstrong, IV; Howard M. Gitten

(57) ABSTRACT

Provided is a decorative tire in which an ink composition including a colorant is directly applied onto the tire surface in order to improve the degree of flexibility in design. This decorative tire has a decorative printed layer formed on the tire surface, the decorative printed layer being a cured film of an active-energy-ray-curable ink composition including a colorant. The ink composition includes a monofunctional monomer having a glass transition point of −30° C. or lower, and a polyfunctional monomer having a glass transition point of 0° C. or lower. Preferably, the ink composition further includes a monofunctional monomer having an alicyclic structure with a glass transition point between 0-110° C. inclusive. Preferably, a surface protection layer that protects the surface of the decorative printed layer is formed on the surface of the decorative printed layer. Also, preferably, a primer layer is formed between the tire surface and the decorative printed layer.

16 Claims, No Drawings

(56) References Cited

FOREIGN PATENT DOCUMENTS

| | | | |
|---|---|---|---|
| JP | 2011162703 A | 8/2011 | |
| WO | WO-2005/026270 A1 | 3/2005 | |
| WO | WO-2008011009 A1 | 1/2008 | |
| WO | WO-2009139455 A1 | 11/2009 | |
| WO | WO-2010/058816 A1 | 5/2010 | |
| WO | WO-2011064977 A1 | 6/2011 | |

OTHER PUBLICATIONS

Office Action for China Patent Application No. 201380005078.6 dated Nov. 24, 2015.

Extended European search report for European Patent Application No. 13735867.7 dated Jul. 13, 2015.

International Search Report for International Application No. PCT/JP2013/050470 dated Apr. 16, 2013.

Office Action for Chinese Patent Application No. 201380005095.X dated Jun. 3, 2015.

International Search Report for PCT/JP2013/050471 dated Apr. 16, 2013.

Office Action for Europe Patent Application No. 13735867.7 dated Apr. 5, 2016.

* cited by examiner

DECORATIVE TIRE AND METHOD FOR PRODUCING SAME

CROSS-REFERENCE TO RELATED APPLICATIONS

This application is the national phase under 35 U.S.C. §371 of PCT International Application No. PCT/JP01231/050471, filed Jan. 11, 2013, which claims the benefit of Japanese Patent Application No, 2012-004527, filed Jan. 12, 2012, the entire contents of the aforementioned applications are hereby incorporated herein by reference.

TECHNICAL FIELD

The present invention relates to a decorative tire having a decorative print layer formed on the tire surface and a method for producing the same.

BACKGROUND ART

Hitherto, in order to enhance the designability of a tire, it has been known that a tire label has been attached to the surface of a sidewall portion of the tire. After attaching the tire label, the surface of the tire repeatedly undergoes great deformation during tire running. Therefore, the tire label is required to have high conformability to the deformation. Conformability means that the base material undergoes expansion and contraction in synchrony with deformation of the base material, without causing cracks due to the deformation (hereinafter, the same). Furthermore, since the tire is used outdoors, it is required that peeling between layers due to temperature change, rainfall, or the like does not occur.

In order to solve such a problem, there is proposed a tire label formed by disposing a paint layer on the surface of a base material and laminating a transparent cover layer to cover the paint layer, the base material layer and the cover layer being formed of an elastic material, in which the hardness of the elastic material forming the base material layer is 20 to 70 according to JIS K6253 and the hardness of the elastic material forming the cover layer is 20 to 100 (refer to Patent Document 1). According to the tire label disclosed in Patent Document 1, it is possible to achieve high conformability to deformation during tire running and to prevent peeling between layers due to temperature change, rainfall, or the like.

(Patent Document 1) Japanese Unexamined Patent Application, Publication No. 2009-280070

DISCLOSURE OF THE INVENTION

Problems to be Solved by the Invention

However, a decorative tire of the related art is formed by attaching a tire label, which has been designed in advance, to a tire having a three-dimensional shape. The degree of freedom of design is restricted and the decorative tire of the related art has been merely a decorative tire formed by putting a mark, such as a mark of a manufacturer, on the sidewall of the tire. To address such a circumstance, a technology of applying an ink composition containing a coloring material directly onto a tire surface and then curing the ink composition has been demanded. In such a case, as described above, since the surface of the tire repeatedly undergoes great deformation during tire running, the cured film of the ink composition is required to have high conformability to the deformation. Furthermore, since the tire is used outdoors, it is required that peeling between layers due to temperature change, rainfall, or the like is prevented.

The present invention was achieved in view of such circumstances, and an object of the present invention is to provide a decorative tire produced by directly applying an ink composition containing a coloring material onto the tire surface in order to increase the degree of freedom of design.

Means for Solving the Problems

The inventors of the present invention conducted a thorough investigation in order to solve the problems described above, and the inventors found that an active-energy-ray-curable ink composition can be applied to a tire surface and a decorative print layer capable of conforming to the deformation of a tire can be satisfactorily formed by investigating the composition of active-energy-ray-polymerizable monomers contained in the active-energy-ray-curable ink composition, thus completing the present invention. Specifically, the present invention provides the following.

(1) The present invention relates to a decorative tire having a decorative print layer formed on the tire surface, the decorative print layer being a cured film of an active-energy-ray-curable ink composition containing a coloring material, in which the active-energy-ray-curable ink composition contains active-energy-ray-polymerizable monomers and an active-energy-ray polymerization initiator, and the ink composition contains, as the active-energy-ray-polymerizable monomers, a monomer A): a monofunctional monomer having a glass transition point of −30° C. or lower, and a monomer B): a polyfunctional monomer having a glass transition point of 0° C. or lower.

(2) Furthermore, the present invention relates to the decorative tire described in (1), in which the ink composition further contains, as the active-energy-ray-polymerizable monomers, a monomer C): a monofunctional monomer having an alicyclic structure having a glass transition point of from 0° C. to 110° C.

(3) Furthermore, the present invention relates to the decorative tire described in (1) or (2), in which when the active-energy-ray-curable ink composition is formed on a rubber base material having an elastic modulus of 1.0 MPa to 1.5 MPa at the time of 100% elongation when a specimen of JIS No. 3 is prepared to be subjected to a tensile test according to JIS K6251, as a cured film having a thickness of 10 μm, and the cured film-formed base material having this cured film formed thereon is used as a specimen of dumbbell-shaped No. 6 (JIS K6251-5) to perform a tensile test according to the method of JIS K7161 at 25° C. and at a tensile rate of 100 mm/min, the decorative print layer formed on the tire surface has a cured film fracture point elongation, at which the cured film undergoes cracking, of 200% or more.

(4) Furthermore, the present invention relates to the decorative tire described in any one of (1) to (3), in which the thickness of the decorative print layer is 1 m to 100 μm.

(5) Furthermore, the present invention relates to the decorative tire described in any one of (1) to (4), in which a surface protective layer that protects the surface of the decorative print layer is formed on the surface of the decorative print layer.

(6) Furthermore, the present invention relates to the decorative tire described in (5), in which the surface protective layer is a cured film produced by applying a silicone-modified (meth)acrylic emulsion and drying the silicone-modified (meth)acrylic emulsion, and the thickness of the surface protective layer is 1 m to 100 m.

(7) Furthermore, the present invention relates to the decorative tire described in any one of (1) to (6), in which a primer layer is formed between the tire surface and the decorative print layer.

(8) Furthermore, the present invention relates to the decorative tire described in any one of (1) to (7), in which the decorative print layer is formed by an inkjet method.

(9) Furthermore, the present invention relates to a method for producing the decorative tire described in any one of (1) to (7), the method including forming the decorative print layer using an inkjet method.

Effects of the Invention

According to the present invention, it is possible to provide a decorative tire in which cracking or peeling does not occur in a decorative print layer (hereinafter, referred to as "decoration" in some cases) even if expansion and contraction is repeated continuously. Furthermore, since decoration is printed directly onto a tire, the degree of freedom of decoration can be increased.

PREFERRED MODE FOR CARRYING OUT THE INVENTION

Hereinafter, specific embodiments of the present invention will be described in detail, but the present invention is not intended to be limited to the following embodiments, and the present invention can be carried out by applying appropriate modifications within the intended scope of the present invention.

Decorative Tire

The decorative tire of the present invention has a decorative print layer formed on the tire surface, the decorative print layer being a cured film of an ink composition containing a coloring material.

Decorative Print Layer

The ink composition that constitutes the decorative print layer is an active-energy-ray-curable ink composition containing a coloring material. When a water-based ink composition is used, it is not preferable from the viewpoints that (i) when printing is performed on a tire, since the surface tension of the ink composition is high, the ink composition may not be appropriately applied onto a base material, (ii) when printing is performed on a tire, since the ink composition contains a water-containing solvent, it takes much time until, the ink composition dries, and (iii) when printing is performed on a tire, since it takes a time until the ink composition dries, a plurality of ink compositions each having a different color is mixed on the tire and thus a clear image may not be formed on the tire surface. When a solvent-based ink composition is used, it is not preferable from the viewpoints that (iv) when printing is performed on a tire, the ink composition may cause the base material to be swollen, (v) when printing is performed on a tire, since the ink composition contains a solvent including a high-boiling point solvent, it takes much time until the ink composition dries, and (vi) when printing is performed on a tire, since it takes a time until the ink composition dries, a plurality of ink compositions each having a different color is mixed on the tire and thus a clear image may not be formed on the tire surface.

The decorative print layer may be printed by any methods such as an inkjet method, a spraying method, or a brush coating method, but the inkjet method is preferable from the viewpoint of increasing the degree of freedom of decoration.

[Active-Energy-Ray-Curable Ink Composition]
[Coloring Material]

The coloring material may be any inorganic pigment or organic pigment that is usually used in conventional oily ink compositions, and examples include carbon black, cadmium red, molybdenum red, chrome yellow, cadmium yellow, titanium yellow, titanium oxide, chromium oxide, viridian, Titanium Cobalt Green, Ultramarine Blue, Prussian Blue, Cobalt Blue, diketopyrrolopyrrole, anthraquinone, benzimidazolone, anthrapyrimidine, azo-based pigments, phthalocyanine-based pigments, quinacridone-based pigments, isoindolinone-based pigments, dioxazine-based pigments, indanthrene-based pigments, perylene-based pigments, perinone-based pigments, thioindigo-based pigments, quinophthalone-based pigments, metal complex pigments, aluminum paste, silica, calcium carbonate, magnesium carbonate, clay, precipitated barium sulfate, and pearl pigment.

A preferred dispersed particle size of the pigment of the active-energy-ray-curable ink composition is preferably from 10 nm to 300 nm as a volume average particle size according to a laser scattering method. If the dispersed particle size is less than 10 nm, since light resistance may be decreased, it is not preferable. On the other hand, if the dispersed particle size is more than 300 nm, stable maintenance of dispersion is made difficult, and when precipitation of the pigment occurs, or the inkjet ink is ejected by an inkjet recording apparatus, head clogging may occur, or ejection bending may occur, which is not preferable.

According to the present invention, when a pigment is used, the content thereof may be appropriately adjusted. The content may vary depending on the kind of the pigment, but from the viewpoint of achieving a balance between dispersibility and coloring power, the content of the pigment in the total amount of the ink composition is preferably 0.1% to 20% by mass, and more preferably 0.2% to 10% by mass, in the case of an organic pigment. Furthermore, from the viewpoint of achieving a balance between dispersibility and coloring power, the content is preferably 1% to 40% by mass, and more preferably 5% to 20% by mass, in the case of an inorganic pigment.

[Viscosity]

The viscosity of the active-energy-ray-curable ink composition is preferably from 5 mPa·s to 20 mPa·s, and more preferably from 5 mPa·s to 15 mPa·s, at 40° C. If the viscosity is less than 5 mPa·s, it is not preferable from the viewpoint that when the ink composition is ejected using an inkjet apparatus, ejectability may be reduced. Ejectability means that dot omission of the ink occurs during continuous printing, or disturbance in ejection or the like occurs, so that printing cannot be carried out normally. If the viscosity exceeds 20 mPa·s, even if a mechanism of decreasing the viscosity by heating is incorporated in the head of the inkjet apparatus, it is not preferable from the viewpoint that ejection failure caused by dot omission occurs, and there is a possibility that the ink composition may not be ejected normally.

Furthermore, from the viewpoint of inkjet ejectability and ejection stability, the surface tension of the active-energy-ray-curable ink composition of the present invention is preferably so that the surface tension at 40° C. is 20 mN/m to 40 mN/m.

[Composition]

In order to increase conformability with respect to the tire, the active-energy-ray-curable ink composition contains active-energy-ray-polymerizable monomers and an active-energy-ray polymerization initiator. The active-energy-ray-polymerizable monomers include a monomer A): a monofunctional monomer having a glass transition point of −30° C. or lower, and a monomer B): a polyfunctional monomer having a glass transition point of 0° C. or lower. Furthermore, in addition to the monomers A) and B), it is more preferable for the active-energy-ray-curable ink composition to contain a monomer C): a monofunctional monomer having an alicyclic structure having a glass transition point of from 0° C. to 110° C.

In the present specification, the term "active-energy-ray-polymerizable monomer" refers to a polymerizable monomer having one or more ethylenically unsaturated double bonds.

[Monomer a): Monofunctional Monomer Having Glass Transition Point of −30° C. or Lower]

The active-energy-ray-polymerizable monofunctional monomers include a monomer A), an active-energy-ray-polymerizable monofunctional monomer having an ethylenically unsaturated double bond, which gives a homopolymer having a glass transition point (Tg) of lower than −30° C. (hereinafter, also referred to as "monomer A)"). The monomer A) can increase flexibility and stretchability of the cured film. Flexibility being high means that when the printed object on which a cured film of the ink composition is formed is bent, the cured film is not easily damaged, and stretchability being high means that when the cured film is pulled, the cured film is not easily breakable (hereinafter, the same).

Examples of the monomer A) include 2-ethylhexyl acrylate (Tg=−85° C.), 2-ethylhexylcarbitol acrylate (Tg=−65° C.), 2-methoxyethyl acrylate (Tg=−50° C.), 2-methoxybutyl acrylate (Tg=−56° C.), 4-hydroxybutyl acrylate (Tg=−80° C.), diethylene glycol monoethyl ether acrylate (Tg=−70° C.), ethoxydiethylene glycol acrylate (Tg=−70° C.), isoamyl acrylate (Tg=−45° C.), isodecyl acrylate (Tg=−55° C.), isooctyl acrylate (Tg=−83° C.), isotetradecyl acrylate (Tg=−56° C.), caprolactone acrylate (Tg=−53° C.), methoxytripropylene glycol acrylate (Tg=−75° C.), EO (ethylene oxide)-modified succinic acid acrylate (Tg=−40° C.), and tridecyl acrylate (Tg=−75° C.). Among them, from the viewpoint of having excellent flexibility and adhesiveness and undergoing curing shrinkage, the monomer A) is preferably any one or more monomers selected from isooctyl acrylate, tridecyl acrylate and ethoxydiethylene glycol acrylate.

The content of the monomer A) is preferably from 2% by mass to 65% by mass, more preferably from 5% by mass to 50% by mass, and even more preferably from 10% by mass to 35% by mass, relative to the total amount of the active-energy-ray-polymerizable monomers. If the content is less than 2% by mass, it is not preferable from the viewpoint that when the ink composition is printed on a tire, the ink composition cannot conform to the elongation of the tire, and cracking or peeling may occur in the cured product of the ink composition. If the content is more than 65% by mass, it is not preferable from the viewpoint that when the ink composition is irradiated with a predetermined amount of active energy radiation, there is the possibility that curing of the ink composition may be insufficient.

[Monomer B): Polyfunctional Monomer Having Glass Transition Point of 0° C. or Lower]

The active-energy-ray-polymerizable polyfunctional monomers include monomer B): a polyfunctional monomer having an ethylenically unsaturated double bond, which gives a homopolymer having a glass transition point of 0° C. or lower (hereinafter, also referred to as "monomer B)"). The monomer B) contributes to an enhancement of curability, and since the glass transition point is low, the monomer B) is well-balanced between "curability" and "flexibility or stretchability". Curability means that since the monomer is polyfunctional, the monomer has high crosslinkability, and can form a cured film with only a small amount of active energy ray irradiation. If Tg is higher than 0° C., it is not preferable from the viewpoint that when printing is performed on a tire, the ink composition cannot conform to the elongation of the tire to be printed, and cracking or peeling may occur in the cured product of the ink composition.

Regarding the monomer B), preferred examples of bifunctional monomers include diacrylates of 11-mole to 32-mole ethylene oxide addition modification products of bisphenol A (hereinafter, referred to as "EO-modified"); polyethylene glycol diacrylates having the number of repetition n of ethylene glycol of 7 to 14; and polypropylene glycol diacrylates having the number of repetition n of propylene glycol of 7 to 1.4. More preferred examples include EO-modified (30) bisphenol A diacrylate (Tg=−42° C.), which is a 30-mole EO addition modification product, polyethylene glycol diacrylate (n=9, Tg=−20° C.), polyethylene glycol diacrylate (n=13 to 14, Tg=−34° C.), polypropylene glycol diacrylate (n=7, Tg=−8° C.), and polypropylene glycol diacrylate (n=12, Tg=−32° C.).

Regarding the monomer B), examples of trifunctional monomers include EO-modified (3) trimethylolpropane triacrylate (Tg=−40° C.), EO-modified (6) trimethylolpropane triacrylate (Tg=−8° C.), EO-modified (9) trimethylolpropane triacrylate (Tg=−19° C.), EO-modified (15) trimethylolpropane triacrylate (Tg=−32° C.), propylene oxide addition modification products (hereinafter, referred to as "PO-modified") (3) trimethylolpropane triacrylate (Tg=−15° C.), and PO-modified (6) trimethylolpropane triacrylate (Tg=−15° C.).

Among the monomers described above, from the viewpoint of having a cured film having excellent flexibility and curability, a bifunctional monomer having a Tg of −30° C. or lower is preferred, and any one or more monomers selected from polypropylene glycol diacrylate (n=12, Tg=−32° C.), polyethylene glycol diacrylate (n=13 to 14, Tg=−34° C.), and EO-modified (30) bisphenol A diacrylates (Tg=−42° C.) are more preferred.

The content of the monomer B) is preferably from 2% by mass to 30% by mass, more preferably from 5% by mass to 15% by mass, and particularly preferably from 9% by mass to 15% by mass, relative to the total amount of the active-energy-ray-polymerizable monomers. If the content is less than 2% by mass, when the ink composition is cured by irradiating the ink composition with active energy radiation, a large amount of irradiation is required, and there is a possibility that curing cannot be sufficiently achieved with a predetermined amount of active energy ray irradiation. If the content is more than 30% by mass, the viscosity increases, and crosslinkability becomes excessively high, so that there is a possibility that conformability or stretchability may decrease.

When both the monomer A) and the monomer B) are incorporated, a good balance can be achieved between "flexibility or stretchability" and "curability". When only the monomer A) or only the monomer B) is used, a balance between "flexibility or stretchability" and "curability" cannot be achieved, and an ink composition conforming to a base material having high stretch or elastic properties, such as a tire, cannot be obtained.

[Monomer C): Monofunctional Monomer Having Alicyclic Structure with Glass Transition Point of from 0° C. to 110° C.]

The active-energy-ray-polymerizable monofunctional monomers include monomer C): a monofunctional monomer having an alicyclic structure, which gives a homopolymer having a glass transition point of from 0° C. to 110° C. (hereinafter, also referred to as "monomer C)"). When a monofunctional monomer having an alicyclic structure is incorporated in an appropriate amount while the glass transition point is maintained in the range described above, flexibility and film strength of the cured film are enhanced in a well-balanced manner.

Examples of the monomer C) include isobornyl acrylate (Tg=94° C.), 4-t-butylcyclohexyl acrylate (Tg=34° C.), cyclohexyl acrylate (Tg=15° C.), and dicyclopentenyloxyethyl acrylate (Tq=14° C.). Among them, from the viewpoint of enhancing the balance between flexibility and film strength, the monomer C) is preferably any one or more monomers selected from isobornyl acrylate, 4-t-butylcyclohexyl acrylate, cyclohexyl acrylate, and dicyclopentenyloxyethyl acrylate.

From the viewpoint of appropriately enhancing the balance between flexibility and film strength, the content of the monomer C) is preferably from 20% by mass to 65% by mass, and more preferably from 25% by mass to 55% by mass, relative to the total amount of the active-energy-ray-polymerizable monomers. If the content is less than 20% by mass, there is a possibility that the film strength of the cured product may be decreased, which is not preferable. If the content is more than 65% by mass, although the film strength is increased, conformability or flexibility of the base material is decreased, and there is a possibility that the balance between the film strength and flexibility may be decreased, which is not preferable.

When the monomer C) is also incorporated in addition to the monomer A) and the monomer B), since the "coating film strength" is increased, consequently a cured film which satisfies all of "flexibility or stretchability", "curability" and "coating film strength" can be obtained.

Furthermore, another monomer may also be appropriately added in addition to the monomers A) to C), to the extent that the object of the present invention can be achieved. For example, a monofunctional monomer that is exemplified by phenoxyethyl acrylate (Tg=−22° C.), lauryl acrylate (Tg=−3° C.), 2-hydroxyethyl acrylate (Tg=−15° C.), stearyl acrylate (Tg=30° C.), dicyclopentenyl acrylate (Tg=120° C.), dicyclopentanyl acrylate (Tg=120° C.), or 1-adamantyl acrylate (Tg=153° C.); or a polyfunctional monomer that is exemplified by 1,4-butanediol diacrylate (Tg=45° C.), tetraethylene glycol diacrylate (Tg=23° C.), dimethyloltricyclodecane diacrylate (Tg=187° C.), trimethylolpropane triacrylate (Tg=62° C.), or pentaerythritol triacrylate (Tg=103° C.) may also be added.

[Active-Energy-Ray-Polymerization Initiator]

The active-energy-ray-curable ink composition contains an active-energy-ray-polymerization initiator. The active energy radiation may be any light radiation such as far-ultraviolet radiation, ultraviolet radiation, near-ultraviolet radiation and infrared radiation; electromagnetic waves such as X-radiation and γ-radiation; an electron beam, a proton beam, and a neutron beam, as long as the active energy radiation is energy radiation that serves as a trigger of a polymerization reaction of a radical, a cation, an anion or the like; however, from the viewpoints of the rate of curing, easily availability of the irradiation apparatus, price and the like, curing by ultraviolet irradiation is preferred. The active-energy-ray-polymerization initiator is not particularly limited as long as the initiator can accelerate a polymerization reaction of a compound having an ethylenically unsaturated double bond in an active-energy-ray-curable ink composition, by irradiation of active energy radiation, and any active-energy-ray-polymerization initiator that is conventionally known can be used. Specific examples of the active-energy-ray-polymerization initiator include, for example, aromatic ketones such as thioxanthone; α-aminoalkylphenones; α-hydroxyketones; acylphosphine oxides; aromatic onium salts; organic peroxides; thio compounds; hexaarylbiimidazole compounds; keto oxime ester compounds; borate compounds; azinium compounds; metallocene compounds, active ester compounds, compounds having carbon-halogen bonds; and alkylamine compounds.

According to the present invention, regarding the active-energy-ray-polymerization initiator, from the viewpoint of accelerating a polymerization reaction and increasing curability, it is preferable to use, among others, one or more selected from the group consisting of acylphosphine oxides, α-hydroxyketones, and α-aminoalkylphenones.

Specific examples of the acylphosphine oxides include bis(2,4,6-trimethylbenzoyl)-phenylphosphine oxide (trade name: IRGACURE 819, manufactured by BASF Japan, Ltd.), bis(2,6-dimethoxybenzoyl)-2,4,4-trimethylpentylphenylphoshpine oxide, and (2,4,6-trimethoxybenzoyl)phosphine oxide (trade name: LUCIRIN TPO, manufactured by BASF Japan, Ltd.).

Specific examples of α-hydroxyketone include 2-hydroxy-1-{4-[4-(2-hydroxy-2-methylpropionyl)benzyl]phenyl}-2-methylpropan-1-one (trade name: IRGACURE 127, manufactured by BASF Japan, Ltd.), 2-hydroxy-4'-hydroxyethoxy-2-methylpropiophenone (trade name: IRGACURE 2959, manufactured by BASF Japan, Ltd.), 1-hydroxycyclohexyl phenyl ketone (trade name: IRGACURE 184, manufactured by BASF Japan, Ltd.), and an oligo{2-hydroxy-2-methyl-1-[4-(1-methylvinyl)phenyl]propanone (for example, trade name: ESACURE ONE, manufactured by Lamberti Group).

Specific examples of α-aminoalkylphenone include 2-benzyl-2-dimethylamino-1-(4-morpholinophenyl)butanone-1 (trade name: IRGACURE 369, manufactured by BASF Japan, Ltd.), and 2-dimethylamino-2-[(4-methylphenyl)methyl]-1-[4-(4-morpholinyl)phenyl]-1-butanone (for example, trade name: IRGACURE 379, manufactured by BASF Japan, Ltd.).

The amount of the active-energy-ray-polymerization initiator may be any amount capable of appropriately initiating the polymerization reaction of an active energy-ray-polymerizable monomer, and the amount is preferably from 1% by mass to 20% by mass, and more preferably from 3% by mass to 20% by mass, relative to the total amount of the active-energy-ray-curable ink composition.

[Dispersant]

It is preferable that the active-energy-ray-curable ink composition contain a dispersant for dispersing the coloring material. An example of the dispersant may be a polymeric dispersant. The main chain of this polymeric dispersant is formed of a polyester-based chain, a polyacrylic chain, a polyurethane-based chain, a polyamine-based chain, a polycaprolactone-based chain or the like, and the polymeric dispersant preferably has, as a side chain, a polar group such as an amino group, a carboxyl group, a sulfone group or a hydroxyl group, or a salt thereof.

Preferred examples of the polymeric dispersant include polyester-based dispersants, and specific examples include "SOLSPERSE 33000", "SOLSPERSE 32000", and "SOLSPERSE 24000" manufactured by Lubrizol Japan, Ltd.; "Disperbyk 168" manufactured by BYK Chemie GmbH; and "AJISPER PB821" manufactured by Ajinomoto Fine-Techno Co., Inc.

The proportion of the polymeric dispersant is preferably, as an active ingredient, from 3 parts by mass to 100 parts by mass, and more preferably from 5 parts by mass to 60 parts by mass, relative to 100 parts by mass of the coloring material. If the proportion is less than 3 parts by mass, the polymeric dispersant cannot disperse the coloring material uniformly, a decrease in the stability of the ink or a decrease in ejectability is possible, which is not preferable. Stability of the ink means stability of the ink properties (for example, viscosity or particle size) obtainable when the ink composition is stored for a long time. If the proportion is more than 100 parts by mass, the proportion of curable components such as polymerizable monomers is relatively reduced so that curability may be decreased, or flexibility of a cured product may be decreased, which is not preferable.

Furthermore, the content of the polymeric dispersant is preferably, as an active ingredient, from 0.1% by mass to 30% by mass, and more preferably from 0.5% by mass to 20% by mass, relative to the total amount of the ink composition. If the content is less than 0.1% by mass, the polymeric dispersant cannot disperse the coloring material uniformly, a decrease in the stability of the ink or a decrease in ejectability is possible, which is not preferable. If the content is more than 30% by mass, the proportion of curable components such as polymerizable monomers is relatively reduced so that curability may be decreased, or flexibility of the cured product may be decreased, which is not preferable.

[Surface Adjusting Agent]

The active-energy-ray-curable ink composition may further include a surface adjusting agent. There are no particular limitations on the surface adjusting agent, but specific examples include "BYK-306", "BYK-333", "BYK-371", and "BYK-377" manufactured by BYK Chemie GmbH, which have dimethylpolysiloxane; "TegoRad 2100", "TegoRad 2200N" and "TegoRad 2300" manufactured by Evonik Degussa Japan Co., Ltd.

The content of the surface adjusting agent is preferably from 0.1% by mass to 1% by mass relative to the total amount of the ink composition. If the content is less than 0.1% by mass, it is not preferable from the viewpoint that the ink has high surface tension, and the wettability to a tire surface is decreased. Good wettability means that when printing is performed on a base material, the ink composition spreads while wetting, without causing cissing. If the content is more than 1% by mass, since the wet tension of the cured product is lowered, it is not preferable from the viewpoint that when a surface protective layer is formed on the surface of the cured product, cissing may occur.

[Other Additives]

Furthermore, the active-energy-ray-curable ink composition may also include, as other additives, various additives such as a plasticizer, a polymerization inhibitor, a photostabilizer, and an oxidation inhibitor. A solvent can be added to the extent that the object of the present invention is achieved, but it is most preferable that the ink composition does not contain a solvent.

[Cured Film of Active-Energy-Ray-Curable Ink Composition]

The thickness of the cured film is preferably from 1 μm to 100 μm. If the thickness is less than 1 μm, the color density of the decorative print layer is lowered, and there is a possibility that designability or decorativeness may be decreased, or a possibility that properties such as adhesiveness or stretchability may be decreased, which is not preferable. If the thickness is more than 100 μm, when active energy radiation is irradiated onto the ink composition, there is a possibility that the ink composition may not be sufficiently cured in a short time, and therefore, it is not preferable.

Regarding the method for measuring the film thickness of the cured film, an ink composition was applied on a PET film (manufactured by Toyobo Co., Ltd., A4300) under the same coating conditions as those used for the cured film thus produced, and the thickness of the cured film thus obtained was measured using a micrometer. Measurement was carried out at 10 sites for one sample, and the average value of these measured values was designated as the average film thickness. The same also applies to the protective layer and primer that will be described below.

When the above-described active-energy-ray-curable ink composition is formed on a rubber base material having an elastic modulus of 1.0 MPa to 1.5 MPa at the time of 100% elongation when a specimen of JIS No. 3 is prepared to be subjected to a tensile test according to JIS K6251, as a cured film having a thickness of 10 μm, and the cured film-formed base material having this cured film formed thereon is used as a specimen of dumbbell-shaped No. 6 (JIS K6251-5) to perform a tensile test according to the method of JIS K7161 at 25° C. and at a tensile rate of 100 mm/min, the minimum elongation ratio at the time when cracking of the cured film occurs is defined as cured film fracture point elongation (calculated from the formula: (length of printed object when cracking occurred in the cured film−original length of printed object)/original length of printed object×100), and the cured film fracture point elongation is preferably 100% or more (for example, the elongation at the time of stretching the base material to a length of two times the original length is indicated as 100%), and more preferably 200% or more, and is even more preferably from 200% to 1000%. When the cured film fracture point elongation is 200% or more, the cured film can sufficiently conform to the elongation of the tire, and even if the tire is subjected to expansion and contraction, cracking or peeling of the cured film formed on the surface of the tire can be further suppressed. On the other hand, the cured film fracture point elongation of more than 1000% makes it difficult to obtain high strength of the cured film.

Surface Protective Layer

Since the decorative tire is exposed to outdoors, the aesthetic aspect or external appearance of the decorative print layer is considerably impaired by dust, dirt, mud, soot, pitch and the like attached thereto. Furthermore, cracks and the like may be generated at the surface of the decorative print layer and gloss is also impaired due to oxidation or deterioration caused by ultraviolet radiation or the like. Here, it is preferable that a surface protective layer be formed on the decorative tire. Incidentally, the surface protective layer is not limited to the case of being formed on the surface of the decorative print layer, and may be formed directly on the surface of the tire base material, or may be formed on the surface of a primer layer formed on the surface of the tire base material, which will be described below.

Examples of the surface protective layer include a cured film formed by applying an overcoat agent on a cured film of the ink composition and drying the overcoat agent; and a film base material laminated on a tire. When the surface protective layer is formed, the surface of the cured film of the ink composition may have tackiness. Tackiness means that tacky adhesiveness is felt when the surface of the cured film is touched by a finger. In the case of using an overcoat agent, it is preferable to include a silicone-modified (meth)acrylic emulsion having a Tg of 50° C. or lower, from the viewpoint of having excellent conformability to the tire, scratch resistance, chemical resistance or the like.

The amount of active ingredient of the silicone-modified (meth)acrylic emulsion of the overcoat agent is preferably 10% to 80%, and more preferably 20% to 60%. If the amount of active ingredient is less than 10%, it is not preferable from the viewpoint that the drying time for forming the protective layer is lengthened, and thus productivity is decreased. If the amount is 80% or more, it is not preferable from the viewpoint of it being possible that it may be difficult to apply the overcoat agent on the tires.

The thickness of the cured film is preferably from 1 μm to 100 μm. If the thickness is less than 1 μm, it is not preferable because there is a possibility that the cured film may not be protected appropriately. If the thickness is more than 100 μm, it is not preferable from the viewpoint that the drying time for forming the protective layer is lengthened, and thus productivity is lowered.

Examples of commercially available products of an ink composition for forming a surface protective layer that includes the silicone-modified (meth)acrylic emulsion include OP-11, OP-13, OP-39, OP-53, and OP-55 (all manufactured by DNP Fine Chemicals Co., Ltd.). All of these are such that the Tg of the silicone-modified (meth)acrylic emulsion included therein is 50° C. or lower, and therefore, the cured film undergoes satisfactory elongation. Furthermore, the cured film has high conformability to the tire base material even under the conditions in which stress is imposed repeatedly.

Primer Layer

In order to increase adhesiveness between the tire surface and the decorative print layer, a primer layer may be formed between the tire surface and the decorative print layer.

Examples of a primer composition that constitutes the primer layer include the silicone-modified (meth)acrylic emulsion described above, and a resin composition containing a chlorinated polyolefin or the like. From the viewpoint of adhesiveness to the tire base material, conformability, adhesiveness to the active-energy-ray-curable ink composition, flexibility and the like, a primer composition containing a silicone-modified (meth)acrylic emulsion having a Tg of 50° C. or lower is preferred. Furthermore, in order to increase adhesiveness, a curing agent may be added to the primer composition.

The amount of active ingredient of the silicone-modified (meth)acrylic emulsion of the primer composition is preferably 10% to 80%, and more preferably 20% to 60%. If the amount of the active ingredient is less than 10%, it is not preferable from the viewpoint that the drying time for forming a primer layer is lengthened, and thus productivity is lowered. If the amount is more than 80%, it is not preferable from the viewpoint that there is a possibility that it may be difficult to apply the primer composition.

Examples of the curing agent include polyisocyanate. The content of the curing agent is preferably from 1 part by mass to 50 parts by mass relative to 100 parts by mass of the primer composition. If the content is less than 1 part by mass, it is not preferable from the viewpoint that there is a possibility that even if a curing agent is added, adhesiveness may not be significantly increased. If the content is more than 50 parts by mass, it is not preferable because there is a possibility that conformability to the tire base material may be reduced.

In the present invention, the base material to be printed is a colored tire. In this case, it is preferable to incorporate a masking pigment such as a white pigment (for example, titanium oxide or the like), an aluminum paste, or a pearl pigment in the primer composition in order to enhance designability or color developability after printing. Particularly, in order to enhance designability or color developability after printing, a primer composition containing titanium oxide is preferred.

When the primer composition contains titanium oxide, the content of titanium oxide is preferably from 1 part by mass to 50 parts by mass relative to 100 parts by mass of the primer composition. If the content is less than 1 part by mass, there is a possibility that designability or color developability after printing may not be enhanced significantly. If the content is more than 50 parts by mass, the proportion of other resin components is decreased, and thus conformability of the cured film or the like may be decreased.

The thickness of the primer layer is preferably from 1 μm to 100 μm. If the thickness is less than 1 μm, it is not preferable from the viewpoint that even if a primer layer is provided, there is the possibility that adhesiveness between the tire surface and the decorative print layer may not be enhanced significantly, or from the viewpoint that there is a possibility that in the case of a primer layer containing a masking pigment, designability or color developability after printing the decorative print layer may not be enhanced significantly. If the thickness is more than 100 μm, it is not preferable from the viewpoint that the drying time for curing the primer composition is lengthened, and thus productivity is lowered.

Examples of commercially available products of the primer composition include PR-12 and PR-13 (both manufactured by DNP Fine Chemicals Co., Ltd.), both containing titanium oxide and a silicone-modified (meth)acrylic emulsion.

Method for Producing Decorative Tire

Production of the decorative tire of the present invention is carried out by printing the active-energy-ray-curable ink composition onto a tire and then curing the ink composition with active energy radiation.

The decorative print layer may be printed by any methods, such as an inkjet method, a spraying method, or a brush coating method, but the inkjet method is preferable from the viewpoint of increasing the degree of freedom of decoration.

The active energy radiation is preferably light having a wavelength region of 200 nm to 450 nm, and more preferably light having a wavelength region of 250 nm to 430 nm. The light source is not particularly limited, and examples include a high pressure mercury lamp, a metal halide lamp, a low pressure mercury lamp, an ultrahigh pressure mercury lamp, an ultraviolet laser, solar light, and an LED lamp. When active energy radiation is irradiated using such a light source so that the cumulative amount of light is 100 mJ/cm$^2$ or more, and preferably 200 mJ/cm$^2$ or more, the ink composition can be instantaneously cured.

Meanwhile, when a surface protective layer or a primer layer is formed on the tire, any method that can uniformly apply the composition may be used, and for example, the method may be any of spray coating; coating using a towel, a sponge, a nonwoven fabric, a tissue paper or the like; dispenser coating, brush coating, gravure printing, flexographic printing, silk screen printing, inkjetting, a thermal transfer method, and the like.

EXAMPLES

Hereinafter, the present invention will be described in more detail by way of Examples, but the present invention is not intended to be limited by these descriptions.

[Preparation of Dispersion]

First, regarding yellow, red, indigo and black colors other than white color, dispersants at the proportions indicated in Table 1-1 and Table 1-2 were dissolved in a monofunctional monomer, and pigments at the proportions indicated in Table 1-1 and Table 1-2 were added thereto. The amount of the monofunctional monomer used herein was adjusted so as to obtain a pigment concentration of 12%. Then, the mixed liquids were dispersed using a paint shaker so that the volume average diameter of the pigment would be 300 nm or less, and thus dispersion mixtures were obtained. The particle size was measured using Microtrac Particle Size Analyzer UPA150

(manufactured by Nikkiso Co., Ltd.), which is a particle size distribution analyzer utilizing a laser scattering method. Furthermore, for a white ink, the same method was carried out except that the pigment concentration was adjusted to be 40%.

[Preparation of Ink Composition]

Subsequently, other raw materials were mixed at the proportions indicated in Tables 1-1 and 1-2, and the mixtures were respectively stirred for one hour while heat was applied at 50° C. Thereafter, it was confirmed that there was no solution residue, the mixtures were returned to room temperature, and then the dispersion that had been prepared in advance was added and stirred for one hour. Thereafter, the mixture was filtered using a membrane filter. Thus, ink compositions of Production Examples 1 to 37 were prepared.

Production Examples 1 to 37

TABLE 1-1

| | | | Tg (° C.) | Production Example | | | | | | | | |
|---|---|---|---|---|---|---|---|---|---|---|---|---|
| | | | | 1 White | 2 White | 3 White | 4 Yellow | 5 Red | 6 Indigo | 7 Black | 8 White | 9 Yellow |
| Pigment | | Azo-nickel complex pigment (YELLOW pigment) | | | | | 3.6 | | | | | 3.6 |
| | | C.I. Pigment Red 122 (MAGENTA pigment) | | | | | | 3.6 | | | | |
| | | C.I. Pigment Blue 15:4 (CYAN pigment) | | | | | | | 2.4 | | | |
| | | Carbon black (BLACK pigment) | | | | | | | | 1.8 | | |
| | | Titanium dioxide (WHITE pigment) | | 12.0 | 12.0 | 12.0 | | | | | 12.0 | |
| Mono-functional monomer | Monomer A | Isooctyl acrylate | −83 | | 25.0 | | | | | | | 25.0 |
| | | Tridecyl acrylate | −75 | 25.0 | | | 25.0 | 25.0 | 25.0 | 25.0 | 25.0 | |
| | | Ethoxydiethylene glycol acrylate | 70 | | | 25.0 | | | | | | |
| | Monomer C | Isobornyl acrylate | 94 | | | | 26.0 | 26.0 | 32.0 | 33.0 | 21.0 | |
| | | 4-t-butylcyclohexyl acrylate | 34 | | | | 10.4 | 10.4 | 7.6 | 5.7 | 8.5 | |
| | | Cyclohexyl acrylate | 16 | | | | | | | | | 36.4 |
| | | Dicyclopentenyloxyethyl acrylate | 10~15 | | | | | | | | | |
| | Others | Phenoxyethyl acrylate | −22 | 39.78 | 39.78 | 39.78 | 10.78 | 10.28 | 11.28 | 10.28 | 10.28 | 10.78 |
| | | Dicyclopentenyl acrylate | 120 | | | | | | | | | |
| Poly-functional monomer | Monomer B | Polypropylene glycol diacrylate (n = 12) | −32 | | 10.0 | | | | | | | 10.0 |
| | | Polyethylene glycol diacrylate (n = 13~14) | −34 | | | 10.0 | | | | | | |
| | | EO-modified (30) bisphenol A diacrylate | −42 | 10.0 | | | 10.0 | 10.0 | 10.0 | 10.0 | 10.0 | |
| | Others | Dimethyloltricyclodecane diacrylate | 187 | | | | | | | | | |
| Photo-initiator | | 2,4,6-Trimethylbenzoyldiphenyl phosphine oxide | | 10.0 | 10.0 | 10.0 | 2.0 | 3.0 | 2.0 | 5.0 | 10.0 | 2.0 |
| | | 2-Dimethylamino-2-(4-methyl-benzyl)-1-(4-morpholin-4-yl-phenyl)butan-1-one | | | | | 4.0 | 3.5 | 4.5 | 4.5 | | 4.0 |
| | | 1-Hydroxycyclohexyl phenyl ketone | | 2.0 | 2.0 | 2.0 | 2.0 | 2.0 | 2.0 | 2.5 | 2.0 | 2.0 |
| Dispersant | | Polymeric dispersant A | | | | | 6.0 | 6.0 | 3.0 | 2.0 | | 6.0 |
| | | Polymeric dispersant B | | 1.0 | 1.0 | 1.0 | | | | | 1.0 | |
| Additives | | Silicone polyether acrylate | | 0.2 | 0.2 | 0.2 | 0.2 | 0.2 | 0.2 | 0.2 | 0.2 | 0.2 |
| Polymerization inhibitor | | Phenothiazine | | 0.02 | 0.02 | 0.02 | 0.02 | 0.02 | 0.02 | 0.02 | 0.02 | 0.02 |
| | | | | 100.00 | 100.00 | 100.00 | 100.00 | 100.00 | 100.00 | 100.00 | 100.00 | 100.00 |

| | | | Tg (° C.) | Production Example | | | | | | | | |
|---|---|---|---|---|---|---|---|---|---|---|---|---|
| | | | | 10 Red | 11 Indigo | 12 Black | 13 White | 14 Yellow | 15 Red | 16 Indigo | 17 Black | 18 White |
| Pigment | | Azo-nickel complex pigment (YELLOW pigment) | | | | | | 3.6 | | | | |
| | | C.I. Pigment Red 122 (MAGENTA pigment) | | 3.6 | | | | | 3.6 | | | |
| | | C.I. Pigment Blue 15:4 (CYAN pigment) | | | 2.4 | | | | | 2.4 | | |
| | | Carbon black (BLACK pigment) | | | | 1.8 | | | | | | |
| | | Titanium dioxide (WHITE pigment) | | | | | 12.0 | | | | | |
| Mono-functional monomer | Monomer A | Isooctyl acrylate | −83 | 25.0 | 25.0 | 25.0 | 25.0 | | | | | |
| | | Tridecyl acrylate | −75 | | | | | | | | | |
| | | Ethoxydiethylene glycol acrylate | 70 | | | | | 25.0 | 25.0 | 25.0 | 25.0 | 25.0 |
| | Monomer C | Isobornyl acrylate | 94 | | | | | | | | | |
| | | 4-t-butylcyclohexyl acrylate | 34 | | | | | | | | | |

TABLE 1-1-continued

| Category | | Component | Tg | 1 | 2 | 3 | 4 | 5 | 6 | 7 | 8 | 9 |
|---|---|---|---|---|---|---|---|---|---|---|---|---|
| | | Cyclohexyl acrylate | 16 | 36.4 | 39.6 | 38.7 | 29.5 | | | | | |
| | | Dicyclopentenyloxyethyl acrylate | 10~15 | | | | | 36.4 | 36.4 | 39.0 | 38.7 | 29.5 |
| | Others | Phenoxyethyl acrylate | −22 | 10.28 | 11.28 | 10.28 | 10.28 | 10.78 | 10.28 | 11.29 | 10.28 | 10.28 |
| | | Dicyclopentenyl acrylate | 120 | | | | | | | | | |
| Polyfunctional monomer | Monomer B | Polypropylene glycol diacrylate (n = 12) | −32 | 10.0 | 10.0 | 10.0 | 10.0 | | | | | |
| | | Polyethylene glycol diacrylate (n = 13~14) | −34 | | | | | 10.0 | 10.0 | 10.0 | 10.0 | 10.0 |
| | | EO-modified (30) bisphenol A diacrylate | −42 | | | | | | | | | |
| | Others | Dimethyloltricyclodecane diacrylate | 187 | | | | | | | | | |
| Photoinitiator | | 2,4,6-Trimethylbenzoyldiphenyl phosphine oxide | | 3.0 | 2.0 | 5.0 | 10.0 | 2.0 | 3.0 | 2.3 | 5.0 | 10.0 |
| | | 2-Dimethylamino-2-(4-methylbenzyl)-1-(4-morpholin-4-yl-phenyl)butan-1-one | | 3.5 | 4.5 | 4.5 | | 4.0 | 3.5 | 4.5 | 4.5 | |
| | | 1-Hydroxycyclohexyl phenyl ketone | | 2.0 | 2.0 | 2.5 | 2.0 | 2.0 | 2.0 | 2.3 | 2.5 | 2.0 |
| Dispersant | | Polymeric dispersant A | | 6.0 | 3.0 | 2.0 | | 6.0 | 6.0 | 3.0 | 2.0 | |
| | | Polymeric dispersant B | | | | | 1.0 | | | | | 1.0 |
| Additives | | Silicone polyether acrylate | | 0.2 | 0.2 | 0.2 | 0.2 | 0.2 | 0.2 | 0.2 | 0.2 | 0.2 |
| Polymerization inhibitor | | Phenothiazine | | 0.02 | 0.02 | 0.02 | 0.02 | 0.02 | 0.02 | 0.02 | 0.02 | 0.02 |
| | | | | 100.00 | 100.00 | 100.00 | 100.00 | 100.00 | 100.00 | 100.00 | 100.00 | 100.00 |

TABLE 1-2

| | | Tg (°C) | 19 White | 20 White | 21 White | 22 White | 23 White | 24 White | 25 White | 26 White | 27 White | 28 White |
|---|---|---|---|---|---|---|---|---|---|---|---|---|
| Pigment | Azo-nickel complex pigment (YELLOW pigment) | | | | | | | | | | | |
| | C.I. Pigment Red 122 (MAGENTA pigment) | | | | | | | | | | | |
| | C.I. Pigment Blue 15:4 (CYAN pigment) | | | | | | | | | | | |
| | Carbon black (BLACK pigment) | | | | | | | | | | | |
| | Titanium dioxide (WHITE pigment) | | 12.0 | 12.0 | 12.0 | 12.0 | 12.0 | 12.0 | 12.0 | 12.0 | 12.0 | 12.0 |
| Monofunctional monomer Monomer A | Isooctyl acrylate | −83 | 4.0 | 35.28 | 25.0 | 25.0 | | | 2.0 | 47.28 | 25.0 | 25.0 |
| | Tridecyl acrylate | 75 | | | | | 25.0 | 25.0 | | | | |
| | Ethoxydiethylene glycol acrylate | −70 | 21.0 | 21.0 | | | | | 21.0 | 9.0 | | |
| Monomer C | Isobornyl acrylate | 94 | 8.5 | 8.5 | | | | | 8.5 | 8.5 | | |
| | 4-t-butylcyclohexyl acrylate | 34 | | | | | | | | | | |
| | Cyclohexyl acrylate | 16 | | | | | | | | | | |
| Others | Dicyclopentenyloxyethyl acrylate | 10–15 | 31.28 | | | | 15.5 | | | | | |
| | Phenoxyethyl acrylate | −22 | | | 16.28 | 5.78 | 24.28 | 39.76 | 33.28 | | 18.28 | 29.5 |
| | Dicyclopentenyl acrylate | 120 | | | 29.5 | 29.5 | | | | | | |
| Polyfunctional monomer Monomer B | Polypropylene glycol diacrylate (n = 12) | −32 | | 4.0 | | 14.5 | | | | | 2.0 | 20.3 |
| | Polyethylene glycol diacrylate (n = 3–14) | −42 | | | | | | | | | | |
| | EO-modified (30) bisphenol A diacrylate | 187 | | | | | | | | | | |
| Others | Dimethyloltricyclodecane diacrylate | | | | | | | | | | | |
| Photoinitiator | 2,4,6-Trimethylbenzoyldiphenyl phosphine oxide | | 10.0 | 10.0 | 10.0 | 10.0 | 10.0 | 10.0 | 10.0 | 10.0 | 10.0 | 10.0 |
| | 2-Dimethylamino-2-(4-methylbenzyl)-1-(4-morpholin-4-yl-phenyl)butan-1-one | | | | | | | | | | | |
| | 1-Hydroxycyclohexyl phenyl ketone | | | | | | | | | | | |
| Dispersant | Polymeric dispersant A | | 2.0 | 2.0 | 2.0 | 2.0 | 2.0 | 2.0 | 2.0 | 2.0 | 2.0 | 2.0 |
| | Polymeric dispersant B | | | | | | | | | | | |
| Additives | Silicone polyether acrylate | | 1.0 | 1.0 | 1.0 | 1.0 | 1.0 | 1.0 | 1.0 | 1.0 | 1.0 | 1.0 |
| Polymerization inhibitor | Phenothiazine | | 0.2 | 0.2 | 0.2 | 0.2 | 0.2 | 0.2 | 0.2 | 0.2 | 0.2 | 0.2 |
| | | | 0.02 | 0.02 | 0.02 | 0.02 | 0.02 | 0.02 | 0.02 | 0.02 | 0.02 | 0.02 |
| | | | 100.00 | 100.00 | 100.00 | 100.00 | 100.00 | 100.00 | 100.00 | 100.00 | 100.00 | 100.00 |

| | | Tg (°C) | 29 White | 30 White | 31 White | 32 White | 33 White | 34 White | 35 White | 36 White | 37 White |
|---|---|---|---|---|---|---|---|---|---|---|---|
| Pigment | Azo-nickel complex pigment (YELLOW pigment) | | | | | | | | | | |
| | C.I. Pigment Red 122 (MAGENTA pigment) | | | | | | | | | | |
| | C.I. Pigment Blue 15:4 (CYAN pigment) | | | | | | | | | | |
| | Carbon black (BLACK pigment) | | | | | | | | | | |
| | Titanium dioxide (WHITE pigment) | | 12.0 | 12.0 | 12.0 | 12.0 | 12.0 | 12.0 | 12.0 | 12.0 | 12.0 |
| Monofunctional monomer Monomer A | Isooctyl acrylate | −83 | | | | | 25.0 | | | 48.6 | |
| | Tridecyl acrylate | 75 | | | | 25.0 | | 25.0 | 48.6 | | |
| | Ethoxydiethylene glycol acrylate | −70 | | | | | | | | | 48.6 |

TABLE 1-2-continued

| Category | Component | (Tg) | Ex.1 | Ex.2 | Ex.3 | Ex.4 | Ex.5 | Ex.6 | Ex.7 | Ex.8 | Ex.9 |
|---|---|---|---|---|---|---|---|---|---|---|---|
| Monomer C | Isobornyl acrylate | 94 | | | | | | | | | |
| | 4-t-butylcyclohexyl acrylate | 34 | 21.0 | | | 21.0 | | | | | |
| | Cyclohexyl acrylate | 16 | 8.5 | 29.5 | 29.5 | 8.5 | 29.5 | 29.5 | | | |
| Others | Dicyclopentenyloxyethyl acrylate | 10~15 | | | | | | | 7.5 | 7.5 | 7.5 |
| | Phenoxyethyl acrylate | −22 | 35.28 | 35.28 | 35.28 | 10.28 | 10.28 | 10.28 | 2.48 | 2.48 | 2.48 |
| | Dicyclopentenyl acrylate | 120 | | | | | | | 7.80 | 7.80 | 7.80 |
| Polyfunctional monomer Monomer B | Polypropylene glycol diacrylate (n = 12) | −32 | | | 10.0 | | | | | | |
| | Polyethylene glycol diacrylate (n = 3~14) | | | 10.0 | | | | | | | |
| Others | EO-modified (30) bisphenol A diacrylate | −42 | 10.0 | | | | | | | | |
| | Dimethyloltricyclodecane diacrylate | 187 | | | | | | | | | |
| Photoinitiator | 2,4,6-Trimethylbenzoyldiphenyl phosphine oxide | | 10.0 | 10.0 | 10.0 | 10.0 | 10.0 | 10.0 | 8.4 | 8.4 | 8.4 |
| | 2-Dimethylamino-2-(4-methylbenzyl)-1-(4-morpholin-4-yl-phenyl)butan-1-one | | 10.0 | 10.0 | 10.0 | 10.0 | 10.0 | 10.0 | 10.0 | 10.0 | 10.0 |
| | 1-Hydroxycyclohexyl phenyl ketone | | | | | | | | | | |
| Dispersant | Polymeric dispersant A | | 2.0 | 2.0 | 2.0 | 2.0 | 2.0 | 2.0 | 2.0 | 2.0 | 2.0 |
| | Polymeric dispersant B | | | | | | | | | | |
| Additives | Silicone polyether acrylate | | 1.0 | 1.0 | 1.0 | 1.0 | 1.0 | 1.0 | 1.0 | 1.0 | 1.0 |
| Polymerization inhibitor | Phenothiazine | | 0.2 | 0.2 | 0.2 | 0.2 | 0.2 | 0.2 | 0.2 | 0.2 | 0.2 |
| | | | 0.02 | 0.02 | 0.02 | 0.02 | 0.02 | 0.02 | 0.02 | 0.02 | 0.02 |
| | Total | | 100.00 | 100.00 | 100.00 | 100.00 | 100.00 | 100.00 | 100.00 | 100.00 | 100.00 |

The details of carbon black, a polymeric dispersant A and a polymeric dispersant B are as follows.

TABLE 2

|  |  | Product name | Manufacturer |
|---|---|---|---|
| Pigment | Carbon black (BLACK pigment) | NEROX 5600 | Manufactured by Evonik Degussa Japan Co., Ltd. |
| Dispersant | Polymeric dispersant A | Disperbyk168 | Manufactured by BYK Chemie GmbH |
|  | Polymeric dispersant B | SOLSPERSE33000 | Manufactured by Lubrizol Japan, Ltd. |

Examples 1 to 40 and Comparative Examples 1 to 17

TABLE 3

| | Decorative print layer composition | | | | Film thickness [μm] | |
|---|---|---|---|---|---|---|
| | First layer | Second layer | Product name | Manufacturer | First layer | Second layer |
| Example 1-28 | Production Example 1-28 | — | — | — | 10 | — |
| Example 29-32 | Production Example 8 | Production Example 4-7 | — | — | 15 | 10 |
| Example 33-36 | Production Example 13 | Production Example 9-12 | — | — | 15 | 10 |
| Example 37-40 | Production Example 18 | Production Example 14-17 | — | — | 15 | 10 |
| Comparative Example 1-9 | Production Example 29-37 | — | — | — | 10 | — |
| Comparative Example 10 | Water-based inkjet ink Yellow | — | ICY52 | Manufactured by Saiko Epson Corporation | 10 | — |
| Comparative Example 11 | Water-based inkjet ink Magenta | — | ICVM52 | Manufactured by Saiko Epson Corporation | 10 | — |
| Comparative Example 12 | Water-based inkjet ink Cyan | — | ICC52 | Manufactured by Saiko Epson Corporation | 10 | — |
| Comparative Example 13 | Water-based inkjet ink Black | — | ICBK52 | Manufactured by Saiko Epson Corporation | 10 | — |
| Comparative Example 14 | Solvent-based inkjet ink Yellow | — | ECO-SOL MAX ESL3-YE | Manufactured by Roland DG Corporation | 10 | — |
| Comparative Example 15 | Solvent-based inkjet ink Magenta | — | ECO-SOL MAX ESL3-MG | Manufactured by Roland DG Corporation | 10 | — |
| Comparative Example 16 | Solvent-based inkjet ink Cyan | — | ECO-SOL MAX ESL3-CY | Manufactured by Roland DG Corporation | 10 | — |
| Comparative Example 17 | Solvent-based inkjet ink Black | — | ECO-SOL MAX ESL3-BK | Manufactured by Roland DG Corporation | 10 | — |

[Production of Printed Object]
1. Production of Printed Objects Related to Examples A printed object was produced using, as a base material, a rubber base material having an elastic modulus of 1.2 MPa at the time of 100% elongation when a specimen of JIS No. 3 is prepared to be subjected to a tensile test according to JIS K6251, in order to submit the printed object to a table evaluation. A composition that constitutes a decorative print layer as indicated in Table 3 was printed on the surface of a rubber base material by an inkjet method under the conditions of a resolution of 720 dpi so that the average film thickness would be a thickness indicated in Table 3 (the layer configuration was as described in Table 4-1 and Table 4-2, and Examples 1 to 34 were produced thereby). The ink compositions were cured using a SubZero system (UV lamp system, manufactured by Integration Technology, Ltd., D valve, power output: 100 W/cm), under the conditions of a cumulative amount of light of 640 mJ/cm$^2$, a peak illuminance of 640 mW/cm$^2$, and a rate of conveyance of 18 m/min. Measurement of the cumulative amount of light and the peak illuminance was carried out using an ultraviolet actinometer, UV-351 (manufactured by Orc Manufacturing Co., Ltd.). Thereby, decorative print layers were produced.

Incidentally, the table evaluation is carried out using the above-described rubber base material.

2. Production of Printed Objects Related to Comparative Examples

Decorative print layers were produced by printing at a resolution of 720 dpi for Comparative Examples.

[Evaluation of Printability of Decorative Print Layer]

Evaluation of printability of the decorative print layer was carried out by evaluations of three items, that is, wettability, swelling of the base material, and image reproducibility. Hereinafter, without being limited to evaluation of printability of the decorative print layer, in regard to evaluations of various items, there are areas where "○ and x"-based evaluations and "○, Δ and x"-based evaluations are carried out, but the ranges of the evaluation results that are practically usable will be defined to be limited to ○ for the "○ and x"-based evaluations, and to ○ and Δ for the "○, Δ and x"-based evaluations.

[Wettability]

In regard to wettability, evaluation was carried out by visually observing whether or not the base material was wetted with the ink composition when the ink composition was dropped onto the base material using a dropper. The results are presented in Tables 4-1 and 4-2. When comparing cases immediately after dropping, 30 seconds after dropping, a sample in which the ink composition spread while wetting was rated as "○", and a sample in which the ink composition did not spread while wetting was rated as "x".

[Swelling of Base Material]

In regard to swelling of the base material, evaluation was carried out by visually observing whether or not the ink composition caused the base material to be swollen when the ink composition was dropped onto the base material using a dropper. The results are presented in Tables 4-1 and 4-2. When the ink composition was wiped off 30 seconds after dropping, a sample which exhibited no change in the external appearance of the base material was rated as "○", and a sample which exhibited change in the external appearance of the base material was rated as "x".

[Image Reproducibility]

In regard to image reproducibility, after the ink composition was printed on the base material by the inkjet method, evaluation was carried out by visually observing whether or not a clear image could be formed without dots of the ink compositions being mixed with each other on the base material. The results are presented in Tables 4-1 and 4-2. A sample in which the ink compositions were not mixed with each other was rated as "○", and a sample in which the ink compositions were mixed with each other was rated as "x".

[Evaluation of Adhesiveness]

Evaluation of adhesiveness was carried out by two cases, that is, absence of cross cut and presence of cross cut.

[Absence of Cross Cut]

In the case of the absence of cross cut, a Cellophane adhesive tape was attached to a decorative print layer after being cured, the surface protective layer and the Cellophane adhesive tape were caused to adhere sufficiently, and then the Cellophane adhesive tape was peeled off at 90°. The extent of adhesion of the surface protective layer to the base material was judged. The results are presented in Tables 4-1 and 4-2. A sample which exhibited no peeling was rated as "○", and a sample which exhibited peeling was rated as "x".

[Presence of Cross Cut]

In the case of presence of cross cut, evaluation was carried out according to ASTM D3359. A coating film after being cured was cross-cut into 100 squares with a 1 mm interval and then the Cellophane adhesive tape was attached to the cross-cut portion. Then, after the coating film and the Cellophane adhesive tape were caused to adhere sufficiently, the Cellophane adhesive tape was peeled off at 900. The extent of adhesion of the coating film to the base material was judged. The results are presented in Tables 4-1 and 4-2. A sample in which the extent of peeling was less than 5% was rated as "○", a sample in which the extent of peeling was more than or equal to 5% and less than 15% was rated as "Δ", and a sample in which the extent of peeling was more than 15% was rated as "x".

[Evaluation of Bending Resistance]

Evaluation of bending resistance was carried out with two types of test, that is, a 90° bending test and a dynamic fatigue test.

[90° Bending Test]

The 90° bending test was carried out by visually evaluating the presence or absence of cracks in a cured film when a printed object of Example or Comparative Example was bent by 90°. The results are presented in Tables 4-1 and 4-2. A sample which exhibited no cracks was rated as "○", a sample which exhibited cracks in a very small portion was rated as "Δ", and a sample which exhibited cracks over the entire surface was rated as "x".

[Dynamic Fatigue Test]

The dynamic fatigue test was carried out by repeating expansion and contraction of ±30% at a speed (4 Hz) of reciprocation of four times a second. The results are presented in Tables 4-1 and 4-2. A sample which exhibited no cracks when the expansion and contraction was repeated 60,000 times or more was rated as "○", a sample which exhibited cracks in a very small portion when the expansion and contraction was repeated 60,000 times was rated as "Δ", and a sample which exhibited cracks when the expansion and contraction was repeated less than 60,000 times was rated as "x".

[Evaluation of Stretchability]

Evaluation of stretchability was carried out as follows. The printed object was used as a specimen of dumbbell-shaped No. 6 (JIS K6251-5) to be elongated up to 200% at 25° C. and at a tensile rate of 100 mm/min according to the method of JIS K7161. Then, the presence or absence of cracks in the coating film was evaluated at that time. The results are presented in Tables 4-1 and 4-2. A sample which exhibited no cracks was rated as "○", a sample which exhibited cracks in some portions was rated as "Δ", and a sample which exhibited cracks over the entire surface was rated as "x". Furthermore, evaluations were carried out on the presence or absence of cracks when the specimen was elongated up to 300% at 25° C. under the same condition and when the specimen was elongated up to 300% at 5° C. under the same condition.

[Evaluation of Water Resistance]

Water resistance was evaluated by immersing a printed object in tap water at room temperature for one week, and by performing the 90° bending test described above while the printed object obtained thereafter was still wet. Furthermore, the printed object was immersed for one week, and the external appearance of the printed object after being dried was evaluated. The results are presented in Tables 4-1 and 4-2. In regard to the 90° bending test, evaluation was performed in the same manner as in the [Evaluation of bending resistance]. Regarding the external appearance, a sample which exhibited no change was rated as "○", a sample which exhibited a change but did not exhibit any peeling of the coating film was rated as "Δ", and a sample which exhibited peeling of the coating film was rated as "x".

Evaluation of Scratch Resistance

Evaluation of scratch resistance was carried out by evaluating the external appearance when a sample was rubbed 100 times in a reciprocating manner with a Polybrush. The results are presented in Tables 4-1 and 4-2. A sample which exhibited no change in the external appearance was rated as "○", a sample which exhibited scratches in the coating film was rated as "Δ", and a sample which exhibited peeling of the coating film was rated as "x".

TABLE 4-1

| | | | | Example | | | | | | | | |
|---|---|---|---|---|---|---|---|---|---|---|---|---|
| | | | | 1 | 2 | 3 | 4 | 5 | 6 | 7 | 8 | 9 |
| Table evaluation | Decorative print layer configuration | Second layer | Production Example No | — | — | — | — | — | — | — | — | — |
| | | | Color | — | — | — | — | — | — | — | — | — |
| | | First layer | Production Example No | 1 | 2 | 3 | 4 | 5 | 6 | 7 | 8 | 9 |
| | | | Color | White | White | White | Yellow | Red | Indigo | Black | White | Yellow |
| | Printability of decorative print layer | Wettability | | ○ | ○ | ○ | ○ | ○ | ○ | ○ | ○ | ○ |
| | | Swelling of base material | | ○ | ○ | ○ | ○ | ○ | ○ | ○ | ○ | ○ |
| | | Image reproducibility | | ○ | ○ | ○ | ○ | ○ | ○ | ○ | ○ | ○ |

TABLE 4-1-continued

| | | | | Example | | | | | | | | | |
|---|---|---|---|---|---|---|---|---|---|---|---|---|---|
| | | | | 1 | 2 | 3 | 4 | 5 | 6 | 7 | 8 | 9 | |
| | Adhesiveness | Absence of cross cut | | ○ | ○ | ○ | ○ | ○ | ○ | ○ | ○ | ○ | |
| | | Presence of cross cut | | ○ | ○ | ○ | ○ | ○ | ○ | ○ | ○ | ○ | |
| | Bending resistance | 90° bending | | ○ | ○ | ○ | ○ | ○ | ○ | ○ | ○ | ○ | |
| | | Dynamic fatigue test | | ○ | ○ | ○ | ○ | ○ | ○ | ○ | ○ | ○ | |
| | Stretchability | 200%/25° C. | | ○ | ○ | ○ | ○ | ○ | ○ | ○ | ○ | ○ | |
| | | 300%/25° C. | | ○ | ○ | ○ | ○ | ○ | ○ | ○ | ○ | ○ | |
| | | 300%/5° C. | | ○ | ○ | ○ | ○ | ○ | ○ | ○ | ○ | ○ | |
| | Water resistance | Bending resistance | | Δ | Δ | Δ | Δ | Δ | Δ | Δ | Δ | Δ | |
| | | External appearance | | Δ | Δ | Δ | Δ | Δ | Δ | Δ | Δ | Δ | |
| | Scratch resistance | Polybrush 100 times | | Δ | Δ | Δ | ○ | ○ | ○ | ○ | ○ | ○ | |

| | | | | Example | | | | | | | | | |
|---|---|---|---|---|---|---|---|---|---|---|---|---|---|
| | | | | 10 | 11 | 12 | 13 | 14 | 15 | 16 | 17 | 18 | 19 |
| Table evaluation | Decorative print layer configuration | Second layer | Production Example No | — | — | — | — | — | — | — | — | — | — |
| | | | Color | — | — | — | — | — | — | — | — | — | — |
| | | First layer | Production Example No | 10 | 11 | 12 | 13 | 14 | 15 | 16 | 17 | 18 | 19 |
| | | | Color | Red | Indigo | Black | White | Yellow | Red | Indigo | Black | White | White |
| | Printability of decorative print layer | Wettability | | ○ | ○ | ○ | ○ | ○ | ○ | ○ | ○ | ○ | ○ |
| | | Swelling of base material | | ○ | ○ | ○ | ○ | ○ | ○ | ○ | ○ | ○ | ○ |
| | | Image reproducibility | | ○ | ○ | ○ | ○ | ○ | ○ | ○ | ○ | ○ | ○ |
| | Adhesiveness | Absence of cross cut | | ○ | ○ | ○ | ○ | ○ | ○ | ○ | ○ | ○ | ○ |
| | | Presence of cross cut | | ○ | ○ | ○ | ○ | ○ | ○ | ○ | ○ | ○ | ○ |
| | Bending resistance | 90° bending | | ○ | ○ | ○ | ○ | ○ | ○ | ○ | ○ | ○ | ○ |
| | | Dynamic fatigue test | | ○ | ○ | ○ | ○ | ○ | ○ | ○ | ○ | ○ | ○ |
| | Stretchability | 200%/25° C. | | ○ | ○ | ○ | ○ | ○ | ○ | ○ | ○ | ○ | ○ |
| | | 300%/25° C. | | ○ | ○ | ○ | ○ | ○ | ○ | ○ | ○ | ○ | ○ |
| | | 300%/5° C. | | ○ | ○ | ○ | ○ | ○ | ○ | ○ | ○ | ○ | ○ |
| | Water resistance | Bending resistance | | Δ | Δ | Δ | Δ | Δ | Δ | Δ | Δ | Δ | Δ |
| | | External appearance | | Δ | Δ | Δ | Δ | Δ | Δ | Δ | Δ | Δ | Δ |
| | Scratch resistance | Polybrush 100 times | | ○ | ○ | ○ | ○ | ○ | ○ | ○ | ○ | ○ | ○ |

| | | | | Example | | | | | | | | |
|---|---|---|---|---|---|---|---|---|---|---|---|---|
| | | | | 20 | 21 | 22 | 23 | 24 | 25 | 26 | 27 | 28 |
| Table evaluation | Decorative print layer configuration | Second layer | Production Example No | — | — | — | — | — | — | — | — | — |
| | | | Color | — | — | — | — | — | — | — | — | — |
| | | First layer | Production Example No | 20 | 21 | 22 | 23 | 24 | 25 | 26 | 27 | 28 |
| | | | Color | White | White | White | White | White | White | White | White | White |
| | Printability of decorative print layer | Wettability | | ○ | ○ | ○ | ○ | ○ | ○ | ○ | ○ | ○ |
| | | Swelling of base material | | ○ | ○ | ○ | ○ | ○ | ○ | ○ | ○ | ○ |
| | | Image reproducibility | | ○ | ○ | ○ | ○ | ○ | ○ | ○ | ○ | ○ |
| | Adhesiveness | Absence of cross cut | | ○ | ○ | ○ | ○ | ○ | ○ | ○ | ○ | ○ |
| | | Presence of cross cut | | ○ | ○ | ○ | ○ | ○ | ○ | ○ | ○ | ○ |
| | Bending resistance | 90° bending | | ○ | ○ | ○ | ○ | ○ | ○ | ○ | ○ | ○ |
| | | Dynamic fatigue test | | ○ | ○ | ○ | ○ | ○ | Δ | ○ | ○ | ○ |
| | Stretchability | 200%/25° C. | | ○ | ○ | ○ | ○ | ○ | Δ | ○ | ○ | ○ |
| | | 300%/25° C. | | ○ | ○ | ○ | ○ | ○ | Δ | ○ | ○ | ○ |
| | | 300%/5° C. | | ○ | ○ | ○ | ○ | ○ | Δ | ○ | ○ | Δ |
| | Water resistance | Bending resistance | | Δ | Δ | Δ | Δ | Δ | Δ | Δ | Δ | Δ |
| | | External appearance | | Δ | Δ | Δ | Δ | Δ | Δ | Δ | Δ | Δ |
| | Scratch resistance | Polybrush 100 times | | ○ | ○ | ○ | ○ | ○ | Δ | Δ | ○ | |

TABLE 4-2

| | | | | Example | | | | | |
|---|---|---|---|---|---|---|---|---|---|
| | | | | 29 | 30 | 31 | 32 | 33 | 34 |
| Table evaluation | Decorative print layer configuration | Second layer | Production Example No | 4 | 5 | 6 | 7 | 9 | 10 |
| | | | Color | Yellow | Red | Indigo | Black | Yellow | Red |
| | | First layer | Production Example No | 8 | 8 | 8 | 8 | 13 | 13 |
| | | | Color | White | White | White | White | White | White |
| | Printability of decorative print layer | Wettability | | ○ | ○ | ○ | ○ | ○ | ○ |
| | | Swelling of base material | | ○ | ○ | ○ | ○ | ○ | ○ |
| | | Image reproducibility | | ○ | ○ | ○ | ○ | ○ | ○ |
| | Adhesiveness | Absence of cross cut | | ○ | ○ | ○ | ○ | ○ | ○ |
| | | Presence of cross cut | | ○ | ○ | ○ | ○ | ○ | ○ |
| | Bending resistance | 90° bending | | ○ | ○ | ○ | ○ | ○ | ○ |
| | | Dynamic fatigue test | | ○ | ○ | ○ | ○ | ○ | ○ |
| | Stretchability | 200%/25° C. | | ○ | ○ | ○ | ○ | ○ | ○ |
| | | 300%/25° C. | | ○ | ○ | ○ | ○ | ○ | ○ |
| | | 300%/5° C. | | ○ | ○ | ○ | ○ | ○ | ○ |
| | Water resistance | Bending resistance | | Δ | Δ | Δ | Δ | Δ | Δ |
| | | External appearance | | Δ | Δ | Δ | Δ | Δ | Δ |
| | Scratch resistance | Polybrush 100 times | | ○ | ○ | ○ | ○ | ○ | ○ |

| | | | | Example | | | | | |
|---|---|---|---|---|---|---|---|---|---|
| | | | | 35 | 36 | 37 | 38 | 39 | 40 |
| Table evaluation | Decorative print layer configuration | Second layer | Production Example No | 11 | 12 | 14 | 15 | 16 | 17 |
| | | | Color | Indigo | Black | Yellow | Red | Indigo | Black |
| | | First layer | Production Example No | 13 | 13 | 18 | 18 | 18 | 18 |
| | | | Color | White | White | White | White | White | White |
| | Printability of decorative print layer | Wettability | | ○ | ○ | ○ | ○ | ○ | ○ |
| | | Swelling of base material | | ○ | ○ | ○ | ○ | ○ | ○ |
| | | Image reproducibility | | ○ | ○ | ○ | ○ | ○ | ○ |
| | Adhesiveness | Absence of cross cut | | ○ | ○ | ○ | ○ | ○ | ○ |
| | | Presence of cross cut | | ○ | ○ | ○ | ○ | ○ | ○ |
| | Bending resistance | 90° bending | | ○ | ○ | ○ | ○ | ○ | ○ |
| | | Dynamic fatigue test | | ○ | ○ | ○ | ○ | ○ | ○ |
| | Stretchability | 200%/25° C. | | ○ | ○ | ○ | ○ | ○ | ○ |
| | | 300%/25° C. | | ○ | ○ | ○ | ○ | ○ | ○ |
| | | 300%/5° C. | | ○ | ○ | ○ | ○ | ○ | ○ |
| | Water resistance | Bending resistance | | Δ | Δ | Δ | Δ | Δ | Δ |
| | | External appearance | | Δ | Δ | Δ | Δ | Δ | Δ |
| | Scratch resistance | Polybrush 100 times | | ○ | ○ | ○ | ○ | ○ | ○ |

| | | | | Comparative Example | | | | |
|---|---|---|---|---|---|---|---|---|
| | | | | 1 | 2 | 3 | 4 | 5 |
| Table evaluation | Decorative print layer configuration | Second layer | Production Example No | — | — | — | — | — |
| | | | Color | — | — | — | — | — |
| | | First layer | Production Example No | 29 | 30 | 31 | 32 | 33 |
| | | | Color | White | White | White | White | White |
| | Printability of decorative print layer | Wettability | | ○ | ○ | ○ | ○ | ○ |
| | | Swelling of base material | | ○ | ○ | ○ | ○ | ○ |
| | | Image reproducibility | | ○ | ○ | ○ | ○ | ○ |
| | Adhesiveness | Absence of cross cut | | ○ | ○ | ○ | ○ | ○ |
| | | Presence of cross cut | | ○ | ○ | ○ | ○ | ○ |
| | Bending resistance | 90° bending | | Δ | Δ | Δ | Δ | Δ |
| | | Dynamic fatigue test | | X | X | X | X | X |
| | Stretchability | 200%/25° C. | | X | X | X | X | X |
| | | 300%/25° C. | | X | X | X | X | X |
| | | 300%/5° C. | | X | X | X | X | X |
| | Water resistance | Bending resistance | | Δ | Δ | Δ | Δ | Δ |
| | | External appearance | | Δ | Δ | Δ | Δ | Δ |
| | Scratch resistance | Polybrush 100 times | | ○ | ○ | ○ | ○ | ○ |

TABLE 4-2-continued

|  |  |  |  |  | Comparative Example | | | |
|--|--|--|--|--|--|--|--|--|
|  |  |  |  |  | 6 | 7 | 8 | 9 |
| Table evaluation | Decorative print layer configuration | Second layer | Production Example No | | — | — | — | — |
|  |  |  | Color | | — | — | — | — |
|  |  | First layer | Production Example No | | 34 | 35 | 36 | 37 |
|  |  |  | Color | | White | White | White | White |
|  | Printability of decorative print layer | Wettability |  | | ○ | ○ | ○ | ○ |
|  |  | Swelling of base material |  | | ○ | ○ | ○ | ○ |
|  |  | Image reproducibility |  | | ○ | ○ | ○ | ○ |
|  | Adhesiveness | Absence of cross cut |  | | ○ | ○ | ○ | ○ |
|  |  | Presence of cross cut |  | | ○ | ○ | ○ | ○ |
|  | Bending resistance | 90° bending |  | | Δ | ○ | ○ | ○ |
|  |  | Dynamic fatigue test |  | | X | X | X | X |
|  | Stretchability | 200%/25° C. |  | | X | X | X | X |
|  |  | 300%/25° C. |  | | X | X | X | X |
|  |  | 300%/5° C. |  | | X | X | X | X |
|  | Water resistance | Bending resistance |  | | Δ | Δ | Δ | Δ |
|  |  | External appearance |  | | Δ | Δ | Δ | Δ |
|  | Scratch resistance | Polybrush 100 times |  | | ○ | ○ | ○ | ○ |

|  |  |  |  |  | Comparative Example | | | |
|--|--|--|--|--|--|--|--|--|
|  |  |  |  |  | 10 | 11 | 12 | 13 |
| Table evaluation | Decorative print layer configuration | Second layer | Production Example No | | — | — | — | — |
|  |  |  | Color | | — | — | — | — |
|  |  | First layer | Production Example No | | Water based ink | | | |
|  |  |  | Color | | Yellow | Red | Indigo | Black |
|  | Printability of decorative print layer | Wettability |  | | X | X | X | X |
|  |  | Swelling of base material |  | | ○ | ○ | ○ | ○ |
|  |  | Image reproducibility |  | | X | X | X | X |
|  | Adhesiveness | Absence of cross cut |  | | X | X | X | X |
|  |  | Presence of cross cut |  | | — | — | — | — |
|  | Bending resistance | 90° bending |  | | X | X | X | X |
|  |  | Dynamic fatigue test |  | | — | — | — | — |
|  | Stretchability | 200%/25° C. |  | |  |  |  |  |
|  |  | 300%/25° C. |  | | X | X | X | X |
|  |  | 300%/5° C. |  | | X | X | X | X |
|  | Water resistance | Bending resistance |  | | — | — | — | — |
|  |  | External appearance |  | | — | — | — | — |
|  | Scratch resistance | Polybrush 100 times |  | | — | — | — | — |

|  |  |  |  |  | Comparative Example | | | |
|--|--|--|--|--|--|--|--|--|
|  |  |  |  |  | 14 | 15 | 16 | 17 |
| Table evaluation | Decorative print layer configuration | Second layer | Production Example No | | — | — | — | — |
|  |  |  | Color | | — | — | — | — |
|  |  | First layer | Production Example No | | Solvent-based ink | | | |
|  |  |  | Color | | Yellow | Red | Indigo | Black |
|  | Printability of decorative print layer | Wettability |  | | ○ | ○ | ○ | ○ |
|  |  | Swelling of base material |  | | X | X | X | X |
|  |  | Image reproducibility |  | | X | X | X | X |
|  | Adhesiveness | Absence of cross cut |  | | X | X | X | X |
|  |  | Presence of cross cut |  | | — | — | — | — |
|  | Bending resistance | 90° bending |  | | ○ | ○ | ○ | ○ |
|  |  | Dynamic fatigue test |  | | — | — | — | — |
|  | Stretchability | 200%/25° C. |  | |  |  |  |  |
|  |  | 300%/25° C. |  | | X | X | X | X |
|  |  | 300%/5° C. |  | | X | X | X | X |
|  | Water resistance | Bending resistance |  | | — | — | — | — |
|  |  | External appearance |  | | — | — | — | — |
|  | Scratch resistance | Polybrush 100 times |  | | — | — | — | — |

It was confirmed that in a decorative tire having a decorative print layer, which is a cured film of an active-energy-ray-curable ink composition containing a monomer A): a monofunctional monomer having a glass transition point of −30° C. or lower, and a monomer B): a polyfunctional monomer having a glass transition point of 0° C. or lower, formed on the tire surface by an inkjet method, even if expansion and contraction is repeated continuously, the occurrence of cracking or peeling in the decoration can be prevented (Examples 1 to 40). Furthermore, since decoration is printed directly onto the tire by an inkjet method, the degree of freedom of decoration can be increased.

It can be seen from Table 4-1 and Table 4-2 that generally the following tendency is shown. Examples 1 to 3 contain the monomer A) and the monomer B), but do not contain the monomer C). As a result, satisfactory results are obtained, but the Examples have inferior scratch resistance compared with the case of containing the monomer C) in addition to the monomer A) and the monomer B) (Examples 4 to 24). Examples 4 to 24 represent cases containing the monomer C) in addition to the monomer A) and the monomer B), and have suitable scratch resistance as compared with the cases containing the monomer A) and the monomer B) only (Examples 1 to 3). Examples 25 to 28 contain the monomer A), monomer B) and monomer C), but since the contents of some of the monomers are close to the upper limit or the lower limit, these Examples are inferior to Examples 4 to 24 in terms of any one of bending resistance, elongation evaluation and curability. Hereinafter, a more detailed explanation will be given.

Regarding bending resistance, it was confirmed that when the amount of the monomer A) is 5% by mass or more relative to the total amount of the active-energy-ray-polymerizable monomers (Examples 1 to 24, 26 to 28 and the like), a satisfactory result is obtained in the dynamic fatigue test as compared with the case when the amount of the monomer A) is less than 5% by mass relative to the total amount of the active-energy-ray-polymerizable monomers (Example 25).

Regarding stretchability, it was confirmed that when the amount of the monomer A) is 5% by mass or more relative to the total amount of active-energy-ray-polymerizable monomers (Examples 1 to 24, 26 to 28 and the like), high stretchability is obtained as compared with the case when the amount of the monomer A) is less than 5% by mass relative to the total amount of active-energy-ray-polymerizable monomers (Example 25). Furthermore, it was confirmed that when the amount of the monomer A) is 5% by mass or more relative to the total amount of active-energy-ray-polymerizable monomers and the amount of the monomer B) is 20% or less relative to the total amount of active-energy-ray-polymerizable monomers (Examples 1 to 24, 26, 27 and the like), high stretchability is obtained at a low temperature (5° C.) as compared with the case when the amount of the monomer B) is more than 20% by mass relative to the total amount of active-energy-ray-polymerizable monomers (Example 28).

Regarding scratch resistance, it was confirmed that when the ink composition also contains a monomer C): a monofunctional monomer having an alicyclic structure having a glass transition point of from 0° C. to 110° C., in addition to the monomer A) and the monomer B) (Examples 4 to 25, and 28), excellent scratch resistance is obtained as compared with the case when the ink composition does not contain the monomer C) (Examples 1 to 3). From this, it can be said that when the monomer C) is added, the cured film has increased strength.

Furthermore, although the description is not presented in Tables, when the content of the monomer A) is more than 35 parts by mass (Example 26) and the content of the monomer B) is 2 parts by mass or less (Example 27), insufficient curing occurred in some portions and thus an appropriate decorative print layer could not be obtained.

In Examples 29 to 40, printing is performed by overlapping inks of a plurality colors. When printing is performed by overlapping inks of a plurality of colors, the layer thickness of the decorative print layer becomes thicker compared with the case of performing printing an ink of a single color only once; however, it was confirmed that even in this case, the various properties are not affected. Furthermore, it was confirmed that there is no difference in the various properties even with overlapping colors. When printing is performed by overlapping inks, it is preferable because color developability and designability are enhanced. Particularly, it is preferable if a white ink is used as an ink for initial printing after platemaking, because color developability or designability of the inks printed thereabove is enhanced.

On the other hand, it was confirmed that when the ink composition does not contain the monomer A), bending resistance and stretchability are deteriorated, and thus when printing is performed on a tire, the cured film cannot conform to the elongation of the tire and cracking or peeling may occur in the cured product of the ink composition (Comparative Examples 1 to 3). Furthermore, it was confirmed that when the ink composition does not contain the monomer B), at least stretchability is deteriorated (Comparative Examples 4 to 9).

In a case when a water-based ink is used for forming a decorative print layer instead of the active-energy-ray-curable ink composition, it was confirmed that it is not preferable from the viewpoints that (i) when printing is performed on a tire, since the surface tension of the ink composition is high, the ink composition may not be appropriately applied onto a base material, (ii) since the ink composition contains a water-containing solvent, when printing is performed on a tire, a large quantity of heat is necessary until the ink composition is cured and it takes much time to dry the ink composition, and thus, a plurality of ink compositions each having a different color is mixed on the tire and a clear image cannot be formed on the tire surface and reproducibility of the image may also be affected, and (iii) since adhesiveness to the tire is low, satisfactory stretchability cannot be obtained (Comparative Examples 10 to 13). Furthermore, when a solvent-based ink composition is used for forming a decorative print layer, it was confirmed that it is not preferable from the viewpoints that (iv) when printing is performed on a tire, the ink composition may cause a base material to be swollen, (v) since the ink composition contains a solvent including a high-boiling point solvent, when printing is performed on a tire, a large quantity of heat is necessary until the ink composition is cured and it takes much time to dry the ink composition, and thus, a plurality of ink compositions each having a different color is mixed on the tire and a clear image cannot be formed on the tire surface and reproducibility of the image may also be affected, and (vi) satisfactory results can be obtained in the 90° bending test, but since adhesiveness to the tire is low, satisfactory stretchability cannot be obtained (Comparative Examples 14 to 17).

Examples 41 to 58 and Reference Examples 1 and 2

TABLE 5-1

|  |  |  |  | Example 41 | Example 42 | Example 43 | Example 44 | Example 45 |
|---|---|---|---|---|---|---|---|---|
| Layer configuration | Surface protective layer |  | Ink | Protective layer-3 | Protective layer-3 | Protective layer-3 | Protective layer-3 | Protective layer-3 |
|  | Decorative print layer | Second layer | Production Example No | — | — | — | — | — |
|  |  |  | Color | — | — | — | — | — |
|  |  | First layer | Production Example No | 1 | 2 | 3 | 8 | 8 |
|  |  |  | Color | White | White | White | White | White |
|  | Primer layer |  | Ink | — | — | — | — | — |
| Film thickness | Surface protective layer |  | Film thickness [μm] | 10 | 10 | 10 | 10 | 10 |
|  | Decorative print layer | Second layer | Film thickness [μm] | — | — | — | — | — |
|  |  | First layer | Film thickness [μm] | 10 | 10 | 10 | 10 | 10 |
|  | Primer layer |  | Film thickness [μm] | — | — | — | — | — |

|  |  |  |  | Example 46 | Example 47 | Example 48 | Example 49 |
|---|---|---|---|---|---|---|---|
| Layer configuration | Surface protective layer |  | Ink | Protective layer-3 | Protective layer-3 | Protective layer-3 | Protective layer-3 |
|  | Decorative print layer | Second layer | Production Example No | — | 6 | 11 | 16 |
|  |  |  | Color | — | Indigo | Indigo | Indigo |
|  |  | First layer | Production Example No | 8 | 8 | 13 | 18 |
|  |  |  | Color | White | White | White | White |
|  | Primer layer |  | Ink | — | — | — | — |
| Film thickness | Surface protective layer |  | Film thickness [μm] | 10 | 10 | 10 | 10 |
|  | Decorative print layer | Second layer | Film thickness [μm] | — | 10 | 10 | 10 |
|  |  | First layer | Film thickness [μm] | 10 | 15 | 15 | 15 |
|  | Primer layer |  | Film thickness [μm] | — | — | — | — |

TABLE 5-2

|  |  |  |  | Example 50 | Example 51 | Example 52 | Example 53 | Example 54 | Example 55 |
|---|---|---|---|---|---|---|---|---|---|
| Layer configuration | Surface protective layer |  | Ink | Protective layer-3 | Protective layer-3 | Protective layer-3 | Protective layer-3 | Protective layer-3 | Protective layer-3 |
|  | Decorative print layer | Second layer | Production Example No | — | — | — | — | — | — |
|  |  |  | Color | — | — | — | — | — | — |
|  |  | First layer | Production Example No | 6 | 6 | 6 | 11 | 11 | 11 |
|  |  |  | Color | Indigo | Indigo | Indigo | Indigo | Indigo | Indigo |
|  | Primer layer |  | Ink | Primer-1 | Primer-2 | Primer-2 | Primer-1 | Primer-2 | Primer-2 |
| Film thickness | Surface protective layer |  | Film thickness [μm] | 10 | 10 | 10 | 10 | 10 | 10 |
|  | Decorative print layer | Second layer | Film thickness [μm] | — | — | — | — | — | — |
|  |  | First layer | Film thickness [μm] | 10 | 10 | 10 | 10 | 10 | 10 |
|  | Primer layer |  | Film thickness [μm] | 10 | 10 | 10 | 10 | 10 | 10 |

|  |  |  | Example 56 | Example 57 | Example 58 | Reference Example 1 | Reference Example 2 |
|---|---|---|---|---|---|---|---|
| Layer configuration | Surface protective layer | Ink | Protective layer-3 | Protective layer-3 | Protective layer-3 | Protective layer-3 | Protective layer-3 |

TABLE 5-2-continued

| | | | | | | | |
|---|---|---|---|---|---|---|---|
| | Decorative print layer | Second layer | Production Example No | — | — | — | — | — |
| | | | Color | — | — | — | — | — |
| | | First layer | Production Example No | 16 | 16 | 16 | — | — |
| | | | Color | Indigo | Indigo | Indigo | — | — |
| | Primer layer | | Ink | Primer-1 | Primer-2 | Primer-2 | — | Primer-2 |
| Film thickness | Surface protective layer | | Film thickness [μm] | 10 | 10 | 10 | 10 | 10 |
| | Decorative print layer | Second layer | Film thickness [μm] | — | — | — | — | — |
| | | First layer | Film thickness [μm] | 10 | 10 | 10 | — | — |
| | Primer layer | | Film thickness [μm] | 10 | 10 | 10 | — | 10 |

The details of the raw materials are as follows.

TABLE 6

| | Trade name | Manufacturer | Details |
|---|---|---|---|
| Surface protective layer-1 | OP-11 | DNP Fine Chemicals Co., Ltd | Silicone-modified acrylic emulsion |
| Surface protective layer-2 | OP-13 | DNP Fine Chemicals Co., Ltd | Silicone-modified acrylic emulsion |
| Surface protective layer-3 | OP-39 | DNP Fine Chemicals Co., Ltd | Silicone-modified acrylic emulsion |
| Primer-1 | PR-12 | DNP Fine Chemicals Co., Ltd | Silicone-modified acrylic emulsion (Containing titanium oxide) |
| Primer-2 | PR-13 | DNP Fine Chemicals Co., Ltd | Silicone-modified acrylic emulsion (Containing titanium oxide) |

[Production of Printed Object]

A printed object was produced using, as a base material, a rubber base material having an elastic modulus of 1.0 MPa to 1.5 MPa at the time of 100% elongation, in order to submit the printed object to a table evaluation. The compositions for constituting primer layers as indicated in Table 5-1 and Table 5-2 were applied onto the rubber base material using a bar coater #20 so that the average film thickness after being dried would be 10 m. Then, the compositions were dried for one minute under the condition of 120° C. A primer layer was obtained through the above-described process.

Subsequently, the composition for constituting a decorative print layer as indicated in Tables 5-1 and 5-2 was printed by an inkjet method on the surface of the primer layer, so that the average film thickness would be the film thickness indicated in Tables 5-1 and 5-2. Then, the ink composition was cured using a SubZero system (UV lamp system, manufactured by Integration Technology, Ltd., D valve, power output 100 W/cm), under the conditions of a cumulative amount of light of 640 mJ/cm$^2$, a peak illuminance of 640 mW/cm$^2$, and a rate of conveyance of 18 m/min. The measurement of the cumulative amount of light and the peak illuminance was carried out using an ultraviolet actinometer, UV-351 (manufactured by Orc Manufacturing Co., Ltd.). Thereby, a decorative print layer was produced.

Subsequently, the composition for constituting a surface protective layer as indicated in Tables 5-1 and 5-2 was applied on the surface of the decorative print layer using a bar coater #20, so that the average film thickness after being dried would be 10 μm. Then, the composition was dried for one minute at 120° C. A surface protective layer was obtained through the process described above, and also, printed objects of Examples 41 to 58 and Reference Examples 1 and 2 were obtained.

Evaluation

For the printed objects described above, in addition to the items evaluated in Example 1 and the like, detergent resistance, chemical resistance, and tackiness were also evaluated. The same items as the items evaluated in Example 1 and the like were evaluated based on the same criteria as described above. New items were evaluated as follows. The results are presented in Table 7.

[Evaluation of Detergent Resistance]

Evaluation of detergent resistance was carried out by evaluations of two items, that is, the external appearance after dropping a detergent and the external appearance after rubbing with a Polybrush.

[External Appearance after Dropping Detergent]

One drop of a detergent A (trade name: Car Shampoo 38000N, manufactured by Sumitomo 3M Limited) was placed on a printed object and then the printed object was left to stand with a lid at room temperature for 60 minutes. After that, the printed object was washed with water. Thereafter, the external appearance of the coating film was evaluated. The results are presented in Table 7. A sample which exhibited no change in the external appearance was rated as "○", a sample which exhibited change in the external appearance but exhibited no peeling of the coating film was rated as "Δ", and a sample which exhibited peeling of the coating film was rated as "x". Moreover, the same evaluation was also carried out by using a tire coating agent A (trade name: Tire & Rubber Dressing 38042N, manufactured by Sumitomo 3M Limited).

[External Appearance after Rubbing with Polybrush]

A printed object was rubbed 100 times with a Polybrush on which the above-described detergent A was put, and then the printed object was washed with water. Thereafter, the external appearance of the coating film was evaluated. The results are presented in Table 7. A sample which exhibited no change in the external appearance was rated as "○", a sample which exhibited change in the external appearance but exhibited no peeling of the coating film was rated as "Δ", and a sample which exhibited peeling of the coating film was rated as "x". Moreover, the same evaluation was also carried out by using a detergent B (trade name: Tire & Wheel Cleaner 38036N, manufactured by Sumitomo 3M Limited).

[Evaluation of Chemical Resistance]

Evaluation of chemical resistance was carried out by evaluating the external appearance after dropping a chemical agent.

One drop of wax (trade name: Polymer Liquid Wax 38026, manufactured by Sumitomo 3M Limited) was placed on a printed object and then the printed object was left to stand with a lid at room temperature for 60 minutes. After that, the printed object was washed with water. Thereafter, the external appearance of the coating film was evaluated. The results are presented in Table 7. A sample which exhibited no change in the external appearance was rated as "○", a sample which exhibited change in the external appearance but exhibited no peeling of the coating film was rated as "Δ", and a sample which exhibited peeling of the coating film was rated as "x". Moreover, the same evaluation was also carried out by using the above-described tire coating agent A, a tire coating agent B (trade name: Black Coating, manufactured by WILLSON Co., LTD.) and a tire coating agent C (trade name: Pure Shine, manufactured by Soft 99 Corporation).

Evaluation of Tackiness

Evaluation of tackiness was carried out at room temperature.

A printed object was left to stand at room temperature, the coating film was touched with a finger, and the presence or absence of stickiness was checked. The results are presented in Table 7. A sample which exhibited no stickiness was rated as "○", and a sample which exhibited stickiness was rated as "x".

Evaluation of Scratch Resistance

Regarding scratch resistance, not only the external appearance on the occasion in which the sample was rubbed 100 times in a reciprocating manner with a Polybrush, but also the external appearance on the occasion in which the sample was rubbed 100 times (in a single direction) with a brass brush, and the external appearance on the occasion in which the coating film was scratched with fingernails at room temperature were also evaluated. The results are presented in Table 7. A sample in which no change was observed in the external appearance was rated as "○", a sample in which scratches were observed in the coating film was rated as "Δ", and a sample in which peeling of the coating film was observed was rated as "x".

TABLE 7

| | | | | Example |||||||||||
|---|---|---|---|---|---|---|---|---|---|---|---|---|---|---|
| | | | | 41 | 42 | 43 | 44 | 45 | 46 | 47 | 48 | 49 | 50 | 51 |
| Table evaluation | Printability of decorative print layer | Wettability | | ○ | ○ | ○ | ○ | ○ | ○ | ○ | ○ | ○ | ○ | ○ |
| | | Swelling of base material | | ○ | ○ | ○ | ○ | ○ | ○ | ○ | ○ | ○ | ○ | ○ |
| | | Quick-drying property | | ○ | ○ | ○ | ○ | ○ | ○ | ○ | ○ | ○ | ○ | ○ |
| | | Image reproducibility | | ○ | ○ | ○ | ○ | ○ | ○ | ○ | ○ | ○ | ○ | ○ |
| | Adhesiveness | Absence of cross cut | | ○ | ○ | ○ | ○ | ○ | ○ | ○ | ○ | ○ | ○ | ○ |
| | | Presence of cross cut | | ○ | ○ | ○ | ○ | ○ | ○ | ○ | ○ | ○ | ○ | ○ |
| | Bending resistance | 90° bending | | ○ | ○ | ○ | ○ | ○ | ○ | ○ | ○ | ○ | ○ | ○ |
| | | Dynamic fatigue test | | ○ | ○ | ○ | ○ | ○ | ○ | ○ | ○ | ○ | ○ | ○ |
| | Stretchability | 300%/25° C. | | ○ | ○ | ○ | ○ | ○ | ○ | ○ | ○ | ○ | ○ | ○ |
| | | 300%/5° C. | | ○ | ○ | ○ | ○ | ○ | ○ | ○ | ○ | ○ | ○ | ○ |
| | Water resistance | Bending resistance | | ○ | ○ | ○ | ○ | ○ | ○ | ○ | ○ | ○ | ○ | ○ |
| | | External appearance | | ○ | ○ | ○ | ○ | ○ | ○ | ○ | ○ | ○ | ○ | ○ |
| | Detergent resistance | External appearance after dropping | Detergent A | ○ | ○ | ○ | ○ | ○ | ○ | ○ | ○ | ○ | ○ | ○ |
| | | | Tire coating agent A | Δ | Δ | Δ | Δ | Δ | Δ | Δ | Δ | Δ | Δ | Δ |
| | | Polybrush friction | Detergent A | ○ | ○ | ○ | ○ | ○ | ○ | ○ | ○ | ○ | ○ | ○ |
| | | | Detergent B | ○ | ○ | ○ | ○ | ○ | ○ | ○ | ○ | ○ | ○ | ○ |
| | Chemical resistance | External appearance after dropping | Wax A | ○ | ○ | ○ | ○ | ○ | ○ | ○ | ○ | ○ | ○ | ○ |
| | | | Tire coating agent A | ○ | ○ | ○ | ○ | ○ | ○ | ○ | ○ | ○ | ○ | ○ |
| | | | Tire coating agent B | ○ | ○ | ○ | ○ | ○ | ○ | ○ | ○ | ○ | ○ | ○ |
| | | | Tire coating agent C | ○ | ○ | ○ | ○ | ○ | ○ | ○ | ○ | ○ | ○ | ○ |
| | Tackiness | Finger touch at room temperature | | ○ | ○ | ○ | ○ | ○ | ○ | ○ | ○ | ○ | ○ | ○ |
| | Scratch resistance | Polybrush 100 times | | ○ | ○ | ○ | ○ | ○ | ○ | ○ | ○ | ○ | ○ | ○ |
| | | Brass brush 100 times | | ○ | ○ | ○ | ○ | ○ | ○ | ○ | ○ | ○ | ○ | ○ |
| | | Fingernail scratch (Room temperature) | | ○ | ○ | ○ | ○ | ○ | ○ | ○ | ○ | ○ | ○ | ○ |

| | | | | Example ||||||| Reference Example ||
|---|---|---|---|---|---|---|---|---|---|---|---|---|
| | | | | 52 | 53 | 54 | 55 | 56 | 57 | 58 | 1 | 2 |
| Table evaluation | Printability of decorative print layer | Wettability | | ○ | ○ | ○ | ○ | ○ | ○ | ○ | ○ | ○ |
| | | Swelling of base material | | ○ | ○ | ○ | ○ | ○ | ○ | ○ | ○ | ○ |
| | | Quick-drying property | | ○ | ○ | ○ | ○ | ○ | ○ | ○ | ○ | ○ |
| | | Image reproducibility | | ○ | ○ | ○ | ○ | ○ | ○ | ○ | ○ | ○ |
| | Adhesiveness | Absence of cross cut | | ○ | ○ | ○ | ○ | ○ | ○ | ○ | ○ | ○ |
| | | Presence of cross cut | | ○ | ○ | ○ | ○ | ○ | ○ | ○ | ○ | ○ |
| | Bending resistance | 90° bending | | ○ | ○ | ○ | ○ | ○ | ○ | ○ | ○ | ○ |
| | | Dynamic fatigue test | | ○ | ○ | ○ | ○ | ○ | ○ | ○ | ○ | ○ |
| | Stretchability | 300%/25° C. | | ○ | ○ | ○ | ○ | ○ | ○ | ○ | ○ | ○ |
| | | 300%/5° C. | | ○ | ○ | ○ | ○ | ○ | ○ | ○ | ○ | ○ |
| | Water resistance | Bending resistance | | ○ | ○ | ○ | ○ | ○ | ○ | ○ | ○ | ○ |
| | | External appearance | | ○ | ○ | ○ | ○ | ○ | ○ | ○ | ○ | ○ |
| | Detergent resistance | External appearance after dropping | Detergent A | ○ | ○ | ○ | ○ | ○ | ○ | ○ | ○ | ○ |
| | | | Tire coating agent A | Δ | Δ | Δ | Δ | Δ | Δ | Δ | Δ | Δ |
| | | Polybrush friction | Detergent A | ○ | ○ | ○ | ○ | ○ | ○ | ○ | ○ | ○ |
| | | | Detergent B | ○ | ○ | ○ | ○ | ○ | ○ | ○ | ○ | ○ |
| | Chemical | External appearance | Wax A | ○ | ○ | ○ | ○ | ○ | ○ | ○ | ○ | ○ |

TABLE 7-continued

| | | | | | | | | | | | |
|---|---|---|---|---|---|---|---|---|---|---|---|
| resistance | after dropping | Tire coating agent A | ○ | ○ | ○ | ○ | ○ | ○ | ○ | ○ | ○ |
| | | Tire coating agent B | ○ | ○ | ○ | ○ | ○ | ○ | ○ | ○ | ○ |
| | | Tire coating agent C | ○ | ○ | ○ | ○ | ○ | ○ | ○ | ○ | ○ |
| Tackiness | | Finger touch at room temperature | ○ | ○ | ○ | ○ | ○ | ○ | ○ | ○ | ○ |
| Scratch resistance | | Polybrush 100 times | ○ | ○ | ○ | ○ | ○ | ○ | ○ | ○ | ○ |
| | | Brass brush 100 times | ○ | ○ | ○ | ○ | ○ | ○ | ○ | ○ | ○ |
| | | Fingernail scratch (Room temperature) | ○ | ○ | ○ | ○ | ○ | ○ | ○ | ○ | ○ |

In regard to Examples 41 to 43, it was confirmed that when a surface protective layer is formed on the surface of the decorative print layer, water resistance, scratch resistance and the like are further enhanced as compared with Examples 1 to 3. Furthermore, in regard to Examples 44 to 46, it was confirmed that when a surface protective layer is formed on the surface of the decorative print layer, water resistance, scratch resistance and the like are further enhanced as compared with Example 8. Furthermore, in regard to Examples 47 to 49, it was confirmed that when a surface protective layer is formed on the surface of the decorative print layer, water resistance, scratch resistance and the like are further enhanced as compared with Examples 31, 35 and 39. Furthermore, in regard to Examples 50 to 58, it was confirmed that even when a primer layer is formed between the tire surface and the decorative print layer, the performance is not deteriorated.

In regard to Examples 53 to 58, it was confirmed that even when the kinds of the monomers included in the ink composition that constituted the decorative print layer were different, the performance was not deteriorated as compared with Examples 50 to 52. Furthermore, it was confirmed that when a surface protective layer was formed, the effect was effective not only for an enhancement of water resistance and scratch resistance (Polybrush), but also for an enhancement of other resistance properties such as detergent resistance and chemical resistance.

Moreover, it was confirmed that, without being limited to the case when a surface protective layer is formed on the surface of decorative print layer, even when a surface protective layer is formed directly on the surface of the tire base material (Reference Example 1) and a surface protective layer is formed on the surface of the primer layer (Reference Example 2), water resistance, detergent resistance, chemical resistance, scratch resistance and the like are satisfactory.

Examples 59 to 76, Reference Examples 3, 4 and Comparative Examples 18 to 26

TABLE 8-1

| | | | | Example 59 | Example 60 | Example 61 | Example 62 | Example 63 |
|---|---|---|---|---|---|---|---|---|
| Layer configuration | Surface protective layer | Ink | | Protective layer-3 | Protective layer-3 | Protective layer-3 | Protective layer-3 | Protective layer-3 |
| | Decorative print layer | Second layer | Production Example No | — | — | — | — | — |
| | | | Color | — | — | — | — | — |
| | | First layer | Production Example No | 1 | 2 | 3 | 5 | 10 |
| | | | Color | White | White | White | White | White |
| | Primer layer | Ink | | — | — | — | — | — |
| | Surface protective layer | | Applying method | Spraying | Spraying | Spraying | Spraying | Spraying |
| | | | Film thickness [μm] | 25 | 25 | 25 | 25 | 25 |
| | Decorative print layer | | Applying method | IJ | IJ | IJ | IJ | IJ |
| | | Second layer | Film thickness [μm] | — | — | — | — | — |
| | | First layer | Film thickness [μm] | 10 | 10 | 10 | 10 | 10 |
| | Primer layer | | Applying method | — | — | — | — | — |
| | | | Film thickness [μm] | — | — | — | — | — |

| | | | | Example 64 | Example 65 | Example 66 | Example 67 |
|---|---|---|---|---|---|---|---|
| Layer configuration | Surface protective layer | Ink | | Protective layer-3 | Protective layer-3 | Protective layer-3 | Protective layer-3 |
| | Decorative print layer | Second layer | Production Example No | — | 3 | 8 | 13 |
| | | | Color | — | Indigo | Indigo | Indigo |
| | | First layer | Production Example No | 15 | 5 | 10 | 15 |
| | | | Color | White | White | White | White |
| | Primer layer | Ink | | — | — | — | — |
| | Surface protective layer | | Applying method | Spraying | Spraying | Spraying | Spraying |
| | | | Film thickness [μm] | 25 | 25 | 25 | 25 |
| | Decorative print layer | | Applying method | IJ | IJ | IJ | IJ |
| | | Second layer | Film thickness [μm] | — | 10 | 10 | 10 |
| | | First layer | Film thickness [μm] | 10 | 15 | 15 | 15 |
| | Primer layer | | Applying method | — | — | — | — |
| | | | Film thickness [μm] | — | — | — | — |

TABLE 8-2

|  |  |  |  | Example 68 | Example 69 | Example 70 | Example 71 | Example 72 | Example 73 |
|---|---|---|---|---|---|---|---|---|---|
| Layer configuration | Surface protective layer | Ink | | Protective layer-1 | Protective layer-2 | Protective layer-3 | Protective layer-1 | Protective layer-2 | Protective layer-3 |
| | Decorative print layer | Second layer | Production Example No Color | — | — | — | — | — | — |
| | | First layer | Production Example No Color | 3 Indigo | 3 Indigo | 3 Indigo | 8 Indigo | 8 Indigo | 8 Indigo |
| | Primer layer | Ink | | Primer-1 | Primer-2 | Primer-2 | Primer-1 | Primer-2 | Primer-2 |
| | Surface protective layer | Applying method Film thickness [μm] | | Spraying 25 | Spraying 25 | Spraying 25 | Spraying 25 | Spraying 25 | Spraying 25 |
| | Decorative print layer | Applying method Second layer Film thickness [μm] First layer Film thickness [μm] | | IJ — 10 | IJ — 10 | IJ — 10 | IJ — 10 | IJ — 10 | IJ — 10 |
| | Primer layer | Applying method Film thickness [μm] | | Spraying 25 | Spraying 25 | Spraying 25 | Spraying 25 | Spraying 25 | Spraying 25 |

|  |  |  |  | Example 74 | Example 75 | Example 76 | Reference Example 3 | Reference Example 4 |
|---|---|---|---|---|---|---|---|---|
| Layer configuration | Surface protective layer | Ink | | Protective layer-1 | Protective layer-2 | Protective layer-3 | Protective layer-3 | Protective layer-3 |
| | Decorative print layer | Second layer | Production Example No Color | — | — | — | — | — |
| | | First layer | Production Example No Color | 13 Indigo | 13 Indigo | 13 Indigo | — | — |
| | Primer layer | Ink | | Primer-1 | Primer-2 | Primer-2 | — | Primer-2 |
| | Surface protective layer | Applying method Film thickness [μm] | | Spraying 25 | Spraying 25 | Spraying 25 | Spraying 25 | Spraying 25 |
| | Decorative print layer | Applying method Second layer Film thickness [μm] First layer Film thickness [μm] | | IJ — 10 | IJ — 10 | IJ — 10 | — — — | — — — |
| | Primer layer | Applying method Film thickness [μm] | | Spraying 25 | Spraying 25 | Spraying 25 | — — | Spraying 25 |

TABLE 8-3

|  |  |  |  | Comparative Example 18 | Comparative Example 19 | Comparative Example 20 | Comparative Example 21 | Comparative Example 22 |
|---|---|---|---|---|---|---|---|---|
| Layer configuration | Surface protective layer | Ink | | Protective layer-3 | Protective layer-3 | Protective layer-3 | Protective layer-3 | Protective layer-3 |
| | Decorative print layer | Second layer | Production Example No Color | — | — | — | — | — |
| | | First layer | Production Example No Color | 29 White | 30 White | 31 White | 32 White | 33 White |
| | Primer layer | Ink | | — | — | — | — | — |
| | Surface protective layer | Applying method Film thickness [μm] | | Spraying 25 | Spraying 25 | Spraying 25 | Spraying 25 | Spraying 25 |
| | Decorative print layer | Applying method Second layer Film thickness [μm] First layer Film thickness [μm] | | IJ — 10 | IJ — 10 | IJ — 10 | IJ — 10 | IJ — 10 |
| | Primer layer | Applying method Film thickness [μm] | | — — | — — | — — | — — | — — |

|  |  |  |  | Comparative Example 23 | Comparative Example 24 | Comparative Example 25 | Comparative Example 26 |
|---|---|---|---|---|---|---|---|
| Layer configuration | Surface protective layer | Ink | | Protective layer-3 | Protective layer-3 | Protective layer-3 | Protective layer-3 |
| | Decorative print layer | Second layer | Production Example No Color | — | — | — | — |
| | | First layer | Production Example No Color | 34 White | 35 White | 36 White | 37 White |
| | Primer layer | Ink | | — | — | — | — |
| | Surface protective layer | Applying method Film thickness [μm] | | Spraying 25 | Spraying 25 | Spraying 25 | Spraying 25 |
| | Decorative print layer | Applying method Second layer Film thickness [μm] First layer Film thickness [μm] | | IJ — 10 | IJ — 10 | IJ — 10 | IJ — 10 |

TABLE 8-3-continued

| | Primer layer | Applying method<br>Film thickness [μm] | — | — | — | — |

[Production of Decorative Tire]

Subsequently, decorative tires of Examples 52 to 68 were produced using a tire (product name: SNWAKER, size: 155/65R13, manufactured by Bridgestone Corporation) as a base material, in order to submit the decorative tires to a drum running test and the like. Each composition for constituting a primer layer as indicated in Table 8-1 to Table 8-3 was applied onto the tire by spray coating so that the average film thickness would be 25 μm. Then, the compositions were dried for two minutes under the condition of 80° C. Primer layers were obtained through the above-described process.

Subsequently, the compositions were printed by an inkjet method on the surfaces of the primer layers, so that layer configurations and film thicknesses of the decorative print layers would be as indicated in Table 8-1 to Table 8-3. Then, the ink compositions were cured using SUBZERO 085 (UV lamp system, manufactured by Integration Technology, Ltd., power output: 100 W/cm), under the conditions of a cumulative amount of light of 200 mJ/cm$^2$ and a peak illuminance of 1200 mW/cm$^2$. Measurement of the cumulative amount of light and the peak illuminance was carried out using an ultraviolet actinometer, Power Pack (manufactured by EIT Inc.). Thereby, a decorative print layer was produced.

Subsequently, each composition for constituting a surface protective layer as indicated in Table 8-1 to Table 8-3 was applied by spray coating onto the surface of the decorative print layer, so that the average film thickness would be 25 μm. Then, the compositions were dried for two minutes under the condition of 80° C. Surface protective layers were obtained through the process described above, and also, decorative tires of Examples 59 to 76 and Reference Examples 3 and 4 were obtained.

[Evaluation of Tire Drum]

The decorative tires were evaluated by performing a drum running test. The tire running test was carried out at a speed of 60 km/h and then the presence or absence of peeling or cracking of the coating film was checked. The results are presented in Table 9. A sample which exhibited no peeling or cracking of the coating film even when running 8,000 km or longer was rated as "O", and a sample which exhibited peeling or cracking of the coating film when running 8,000 km or shorter was rated as "x".

functional monomer having a glass transition point of −30° C. or lower, and a monomer B): a polyfunctional monomer having a glass transition point of 0° C. or lower, formed on the tire surface by an inkjet method, even if the tire is caused to run for a long time, the occurrence of cracking or peeling in the decoration can be prevented (Examples 59 to 76). Furthermore, it was confirmed that, even when the surface protective layer is not formed on the surface of the decorative print layer but formed directly on the surface of the tire base material (Reference Example 3) and formed on the surface of the primer layer (Reference Example 4), the result of the running test for a long time is satisfactory.

On the other hand, it was confirmed that, in all of the cases where the monomer A) is not contained (Comparative Examples 18 to 20) and the monomer B) is not contained (Comparative Examples 21 to 26) as the active-energy-ray-polymerizable monomers, if the tire is caused to run for a long time, cracking or peeling may occur in the decoration, which is not desirable.

The invention claimed is:

1. A decorative tire having a decorative print layer formed on a tire surface, the decorative print layer being a cured film of an active-energy-ray-curable ink composition containing a coloring material,
   wherein the active-energy-ray-curable ink composition contains active-energy-ray-polymerizable monomers and an active-energy-ray polymerization initiator, and
   the ink composition contains, as the active-energy-ray-polymerizable monomers,
   a monomer A): a monofunctional monomer having a glass transition point of −30° C. or lower,
   a monomer B): a polyfunctional monomer having a glass transition point of 0° C. or lower,
   wherein a primer layer is formed between the tire surface and the decorative print layer, and
   a thickness of the primer layer is 25 μm to 100 μm.

2. The decorative tire according to claim 1, wherein the ink composition further contains, as the active-energy-ray-polymerizable monomers,
   a monomer C): a monofunctional monomer having an alicyclic structure having a glass transition point of from 0° C. to 110° C.

TABLE 9

| | | | Example | | | | | | | | | | | | | |
|---|---|---|---|---|---|---|---|---|---|---|---|---|---|---|---|---|
| | | | 59 | 60 | 61 | 62 | 63 | 64 | 65 | 66 | 67 | 68 | 69 | 70 | 71 | 72 | 73 |
| Tire evaluation | Tire drum evaluation | 8000 km or longer | O | O | O | O | O | O | O | O | O | O | O | O | O | O | O |

| | | | Example | | | Reference Example | | Comparative Example | | | | | | | | |
|---|---|---|---|---|---|---|---|---|---|---|---|---|---|---|---|---|
| | | | 74 | 75 | 76 | 3 | 4 | 18 | 19 | 20 | 21 | 22 | 23 | 24 | 25 | 26 |
| Tire evaluation | Tire drum evaluation | 8000 km or longer | O | O | O | O | O | x | x | x | x | x | x | x | x | x |

It was confirmed that in a decorative tire having a decorative print layer, which is a cured film of an active-energy-ray-curable ink composition containing a monomer A): a mono- 3. The decorative tire according to claim 1, wherein when the active-energy-ray-curable ink composition is formed on a rubber base material having an elastic modulus of 1.0 Mpa to 1.5 MPa at the time of 100% elongation when a specimen of JIS number 3 is prepared to be subjected to a tensile test according to JIS K6251, as a cured film having a thickness of 10 μm, and the cured film-formed base material having the cured film formed thereon is used as a specimen of dumbbell-shaped number 6 (JIS K6251-5) to perform a tensile test according to the method of JIS K7161 at 25° C. and at a tensile rate of 100 mm/min, the decorative print layer formed on the tire surface has a cured film fracture point elongation, at which the cured film undergoes cracking, of 200% or more.

4. The decorative tire according to claim 1, wherein a thickness of the decorative print layer is 1 μm to 100 μm.

5. The decorative tire according to claim 1, wherein a surface protective layer that protects a surface of the decorative print layer is formed on the surface of the decorative print layer.

6. The decorative tire according to claim 5, wherein the surface protective layer is a cured film produced by applying a silicone-modified (meth)acrylic emulsion and drying the silicone-modified (meth)acrylic emulsion, and a thickness of the surface protective layer is 1 μm to 100 μm.

7. The decorative tire according to claim 1, wherein the decorative print layer is formed by an inkjet method.

8. A method for producing the decorative tire according to claim 1, the method comprising forming the decorative print layer by an inkjet method.

9. The decorative tire according to claim 2, wherein when the active-energy-ray-curable ink composition is formed on a rubber base material having an elastic modulus of 1.0 Mpa to 1.5 MPa at the time of 100% elongation when a specimen of JIS number 3 is prepared to be subjected to a tensile test according to JIS K6251, as a cured film having a thickness of 10 μm, and the cured film-formed base material having the cured film formed thereon is used as a specimen of dumbbell-shaped number 6 (JIS K6251-5) to perform a tensile test according to the method of JIS K7161 at 25° C. and at a tensile rate of 100 mm/min, the decorative print layer formed on the tire surface has a cured film fracture point elongation, at which the cured film undergoes cracking, of 200% or more.

10. The decorative tire according to claim 2, wherein a thickness of the decorative print layer is 1 μm to 100 μm.

11. The decorative tire according to claim 3, wherein a thickness of the decorative print layer is 1 μm to 100 μm.

12. The decorative tire according to claim 2, wherein a surface protective layer that protects a surface of the decorative print layer is formed on the surface of the decorative print layer.

13. The decorative tire according to claim 3, wherein a surface protective layer that protects a surface of the decorative print layer is formed on the surface of the decorative print layer.

14. The decorative tire according to claim 4, wherein a surface protective layer that protects a surface of the decorative print layer is formed on the surface of the decorative print layer.

15. The decorative tire according to claim 4, wherein the decorative print layer is formed by an inkjet method.

16. The decorative tire according to claim 2, wherein the decorative print layer is formed by an inkjet method.

\* \* \* \* \*